US011224632B2

(12) United States Patent
Willbold et al.

(10) Patent No.: US 11,224,632 B2
(45) Date of Patent: Jan. 18, 2022

(54) METHODS OF TREATING CHRONIC AND NEUROPATHIC PAIN MEDIATED BY N-TYPE NEURONAL CALCIUM CHANNELS USING D-ENANTIOMERIC PEPTIDES

(71) Applicant: FORSCHUNGSZENTRUM JUELICH GMBH, Juelich (DE)

(72) Inventors: Dieter Willbold, Juelich (DE); Dagmar Juergens, Aachen (DE); Janine Kutzsche, Dueren (DE); Gustavo Adolfo Guzman Castro, Duesseldorf (DE); Patricia Hidalgo Jimenez, Juelich (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 16/470,616

(22) PCT Filed: Dec. 21, 2017

(86) PCT No.: PCT/EP2017/084199
§ 371 (c)(1),
(2) Date: Jun. 18, 2019

(87) PCT Pub. No.: WO2018/115341
PCT Pub. Date: Jun. 28, 2018

(65) Prior Publication Data
US 2019/0314447 A1 Oct. 17, 2019

(30) Foreign Application Priority Data
Dec. 23, 2016 (DE) .................. 102016125645.5

(51) Int. Cl.
| | | |
|---|---|---|
| A61K 38/10 | (2006.01) | |
| A61K 38/12 | (2006.01) | |
| C07K 7/00 | (2006.01) | |
| C07K 7/08 | (2006.01) | |
| C07K 7/50 | (2006.01) | |
| C07K 9/00 | (2006.01) | |
| C07K 11/00 | (2006.01) | |
| A61K 9/00 | (2006.01) | |
| A61K 38/17 | (2006.01) | |
| A61P 25/04 | (2006.01) | |
| A61P 25/02 | (2006.01) | |
| A61P 25/00 | (2006.01) | |
| A61P 25/06 | (2006.01) | |
| A61P 25/28 | (2006.01) | |
| C07K 11/02 | (2006.01) | |
| C07K 7/64 | (2006.01) | |

(52) U.S. Cl.
CPC ............ *A61K 38/10* (2013.01); *A61K 9/0053* (2013.01); *A61K 38/12* (2013.01); *A61K 38/17* (2013.01); *A61K 38/1787* (2013.01); *A61P 25/00* (2018.01); *A61P 25/02* (2018.01); *A61P 25/04* (2018.01); *C07K 7/00* (2013.01); *C07K 7/08* (2013.01); *C07K 9/00* (2013.01); *C07K 11/00* (2013.01); *A61P 25/06* (2018.01); *A61P 25/28* (2018.01); *C07K 7/50* (2013.01); *C07K 7/64* (2013.01); *C07K 11/02* (2013.01)

(58) Field of Classification Search
CPC ............ A61K 2300/00; A61K 2800/54; A61K 38/10; A61K 38/12; A61K 9/1271; A61K 38/00; A61P 29/00; A61P 25/04; H01M 10/0565; Y10S 977/773; Y10S 977/906; Y10S 977/907; Y10T 428/254; Y10T 428/2991
See application file for complete search history.

(56) References Cited

U.S. PATENT DOCUMENTS

| | | | | |
|---|---|---|---|---|
| 9,464,118 | B2 * | 10/2016 | Willbold | ................ C07K 7/08 |
| 10,167,318 | B2 * | 1/2019 | Willbold | ............ G01N 33/6896 |
| 10,174,097 | B2 * | 1/2019 | Willbold | ............ C07K 14/4713 |
| 10,239,923 | B2 * | 3/2019 | Willbold | ................ C07K 7/08 |
| 10,428,127 | B2 * | 10/2019 | Willbold | ............ G01N 33/6896 |
| 2012/0329717 | A1 | 12/2012 | Lewis et al. | |
| 2015/0073123 | A1 | 3/2015 | Vlasov et al. | |
| 2015/0119336 | A1 * | 4/2015 | Willbold | ............ G01N 33/6896 |
| | | | | 514/17.8 |
| 2016/0122401 | A1 | 5/2016 | Funke et al. | |
| 2016/0297852 | A1 | 10/2016 | Willbold | |

(Continued)

FOREIGN PATENT DOCUMENTS

| | | | | |
|---|---|---|---|---|
| DE | 102005049537 | * | 4/2007 | ............... C07K 7/64 |
| DE | 102012102998 | A1 | 10/2013 | |

(Continued)

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Alaoui-lsmaili et al., Cytokine Growth Factor Rev. 2009; 20:501-507.*
Guo et al., PNAS 2004; 101:9205-9210.*
McGivern, DDT, 2006; 11: 245-253.*
Alles et al. Pharmcol. Rev. 2018; 70:315-347.*
Striessing PNAS; 2018; 115:12848-12850.*

(Continued)

*Primary Examiner* — Chang-Yu Wang
(74) *Attorney, Agent, or Firm* — Abel Schillinger, LLP

(57) ABSTRACT

The present invention relates to a composition consisting of or containing peptides selected from the group consisting of or containing RD2, D3, homologs having at least 50% identity and derivatives of RD2 or D3 and also polymers containing or consisting of RD2/D3 homologs having at least 50% identity and derivatives of RD2 and under D3 for use as an analgesic, for use in pain therapy, for use in the treatment of chronic and/or neuropathic pain and/or for inhibiting N-type neuronal calcium channels (NCCs).

16 Claims, 14 Drawing Sheets
Specification includes a Sequence Listing.

(56) References Cited

U.S. PATENT DOCUMENTS

| | | | |
|---|---|---|---|
| 2016/0376335 A1* | 12/2016 | Willbold | C07K 7/06 514/17.8 |
| 2018/0044398 A1* | 2/2018 | Willbold | C07K 14/705 |
| 2019/0085030 A1* | 3/2019 | Willbold | C07K 14/4711 |

FOREIGN PATENT DOCUMENTS

| | | | | |
|---|---|---|---|---|
| DE | 102015003676 A1 | 9/2016 | | |
| RU | 2508295 C2 | 9/2013 | | |
| WO | WO0236569 | * | 5/2002 | C07D 215/42 |
| WO | 32081505 A2 | 10/2002 | | |
| WO | 2011032233 A1 | 3/2011 | | |
| WO | 2014177127 A1 | 11/2014 | | |
| WO | 2015043567 A1 | 4/2015 | | |
| WO | WO2016150415 | * | 9/2016 | C07K 7/08 |

OTHER PUBLICATIONS

Nimmrich et al., Br. J. Pharmacol. 2013; 169:1203-1210.*
Tan et al., Neural Regen. Res. 2012; 7:137-140. Doi:10.3969/j.issn.1673-5374.2012.02.010:10.3969/j.issn.1673-5374.2012.*
Morton et al. Laboratory Animals, 2001; 35:1-41, retrieved from the website: journals.sagepub.com/doi/pdf/10.1258/0023677011911345 on Dec. 23, 2019.*
Mittal et al. Drug Deliv. 2014; 21:75-86.*
DE102005049537—English translated version published Apr. 26, 2007.*
Kooten et al. Dement & Geriatr. Cogn. Dis. 2016; 41:220-232.*
Cao et al. J. Neuroinflam. 2019; 16:204.doi.org/10.1186/s12974-019-1608-z.*
Needleman, S.B. et al., J. Mol. Biol. (1970) 48, pp. 445-453.
English language translation of Berezov, T.T. et al., Biological Chemistry, Third Edition, 1998, pp. 34, 59.
Vink, S. et al., British Journal of Pharmacology (2012) 167, pp. 970-989.

* cited by examiner

METHODS OF TREATING CHRONIC AND NEUROPATHIC PAIN MEDIATED BY N-TYPE NEURONAL CALCIUM CHANNELS USING D-ENANTIOMERIC PEPTIDES

The instant application contains a Sequence Listing which has been submitted electronically in ASCII format and is hereby incorporated by reference in its entirety. Said ASCII copy, created on May 19, 2020, is named 6509-P50508_SL.txt and is 9,168 bytes in size.

BACKGROUND OF THE INVENTION

Field of the Invention

The present invention relates to a composition consisting of or containing peptides selected from the group consisting of or containing RD2 of amino acid sequence ptlhthnrrrrr (SEQ ID NO: 1), D3 of amino acid sequence rprtrlhthrnr (SEQ ID NO: 2), homologs having at least 50% identity and derivatives of RD2 (SEQ ID NO: 1) or D3 (SEQ ID NO: 2) and also polymers containing or consisting of RD2/D3 (SEQ ID NO: 1)/(SEQ ID NO: 2) homologs having at least 50% identity and derivatives of RD2 (SEQ ID NO: 1) and D3 (SEQ ID NO: 2) for use as an analgesic, for use in pain therapy, for use in the treatment of chronic and/or neuropathic pain and/or for inhibiting N-type neuronal calcium channels (NCCs). The invention further relates to a method for reducing the release of neurotransmitters compared to a control and also a method for inhibiting an N-type NCC using the above-defined composition.

Discussion of Background Information

Statistics of the German Society for the Study of Pain show that more than 12 million people in Germany suffer from prolonged, chronic pain and/or neuropathic pain. Neuropathic pain occurs following damage to or disease of afferent systems in the peripheral or central nervous system. Although drug therapy allows the pain to be reduced by 50-80%, it is often impossible to achieve complete freedom from pain. Among all drug therapeutic options, approx. 20-40% of patients respond to treatment only to an insufficient degree (<30% pain reduction, so-called non-responders) or suffer from intolerable adverse effects.

In addition to antidepressants (tri/tetracyclic antidepressants, selective serotonin/norepinephrine reuptake inhibitors), long-acting opioids, anticonvulsants that act on the neuronal sodium channels (e.g. carbamazepine) and topical therapeutics (lidocaine patches, high-dose capsaicin patches), pharmacological therapies are used that exert an action on the neuronal calcium channels, such as gabapentin, pregabalin and ziconotide (Prialt®). Gabapentin and pregabalin are specific P/Q-type calcium channel inhibitors, and ziconotide is the only approved specific N-type calcium channel inhibitor. Ziconotide is a cyclic peptide composed of 25 amino acids and was originally isolated from the venom of the cone snail *Conus magus* as ω-conotoxin MVIIA.

Ziconotide is used in patients who suffer from extremely severe pain and in whom all other therapeutic options are unsuccessful. The approval of Prialt® is based on the results of three phase III clinical trials with more than 1200 patients. In all of the studies, ziconotide favorably reduced pain compared to placebo, including highly treatment-refractory chronic pain resulting from cancer or AIDS. Among other benefits, the additional intrathecal administration of ziconotide made it possible to reduce the required dose of opioids. Ziconotide causes fewer adverse effects than morphine.

However, intrathecal (i.t.) administration of ziconotide entails the risk of serious infections such as meningitis that can be fatal. Meningitis due to the penetration of organisms along the catheter or inadvertent contamination of the infusion system is a known complication of intrathecal drug administration, in particular using external systems. Moreover, in 88% of patients, ziconotide causes severe CNS adverse effects such as dizziness, nausea, confusion, unsteady gait, memory disturbances, blurred vision, headache, weakness, vomiting, and somnolence. Despite its highly complex and risky administration route and severe adverse effects, ziconotide is used for pain therapy because it is the only approved specific N-type calcium channel inhibitor that has proven successful even in cases of highly severe pain, caused for example by tumors or AIDS, in which even morphine no longer provides relief.

The object of the present invention is to overcome the drawbacks of the prior art. In particular, the aim is to provide compositions that have fewer adverse effects, specifically and selectively inhibit N-type NCCs in a corresponding manner, and have no effect on the function of the L-type NCCs. The compositions to be provided are to be administrable in a simple manner, preferably by oral administration. Moreover, inhibition of the N-type NCCs is to be reversible in order to prevent long-lasting pain insensitivity and damage. An $IC_{50}$ value above the picomolar range would also be desirable in order to allow administration that is independent of the specific metabolism of the recipient organism. At $IC_{50}$ values in the picomolar range or below, even small changes in the concentration of an active compound have significant impact. This can easily result in underdosing or overdosing, which can depend respectively on specific metabolism and can lead to undesired adverse effects or long-term damage.

A further object is to provide a composition comprising active compounds that ensure passage of the blood-brain barrier.

A further object is to provide stable enteral, intravenous, subcutaneous, intraperitoneal, intranasal and/or oral administration of compositions that manifest this action at the target site, the N-type NCCs.

SUMMARY OF THE INVENTION

This object is achieved in an embodiment by a composition consisting of or containing peptides selected from the group consisting of or containing RD2 (SEQ ID NO: 1), D3 (SEQ ID NO: 2), homologs having at least 50% identity and derivatives of RD2 (SEQ ID NO: 1) or D3 (SEQ ID NO: 2) and also polymers comprising or consisting of RD2, D3, homologs having at least 50% identity and derivatives of RD2 (SEQ ID NO: 1) and D3 (SEQ ID NO: 2) for use as an analgesic.

Further subject matter of the present invention is a composition consisting of or containing peptides selected from the group consisting of or containing RD2 (SEQ ID NO: 1), D3 (SEQ ID NO: 2), homologs having at least 50% identity and derivatives of RD2 (SEQ ID NO: 1) or D3 (SEQ ID NO: 2) and also polymers containing or consisting of RD2 (SEQ ID NO: 1), D3 (SEQ ID NO: 2), homologs having at least 50% identity and derivatives of RD2 (SEQ ID NO: 1) and D3 (SEQ ID NO: 2) for use for use in pain therapy.

Further subject matter of the invention is a composition consisting of or containing peptides selected from the group consisting of or containing RD2 (SEQ ID NO: 1), D3 (SEQ ID NO: 2), homologs having at least 50% identity and derivatives of RD2 (SEQ ID NO: 1) or D3 (SEQ ID NO: 2) and also polymers containing or consisting of RD2 (SEQ ID NO: 1), D3 (SEQ ID NO: 2), homologs having at least 50% identity and derivatives of RD2 (SEQ ID NO: 1) and D3 (SEQ ID NO: 2) for use in the treatment of chronic and/or neuropathic pain.

Further subject matter of the invention is a composition consisting of or containing peptides selected from the group consisting of or containing RD2 (SEQ ID NO: 1), D3 (SEQ ID NO: 2), homologs having at least 50% identity and derivatives of RD2 (SEQ ID NO: 1) or D3 (SEQ ID NO: 2) and also polymers containing or consisting of RD2 (SEQ ID NO: 1), D3 (SEQ ID NO: 2), homologs having at least 50% identity and derivatives of RD2 (SEQ ID NO: 1) and D3 (SEQ ID NO: 2) for inhibiting N-type neuronal calcium channels (NCCs).

In an embodiment of the present invention, the peptide is composed essentially of D-amino acids. Within the meaning of the present invention, the term "essentially of D-amino acids" means that the peptides to be used according to the invention comprise at least 50%, 60%, preferably 75%, 80, 81, 82, 83, 84%, particularly preferably 85, 86, 87, 88, 89%, 90, 91, 92, 93, 94, 95%, and in particular 96%, 97%, 98%, 99%, or 100% D-amino acids or are composed thereof.

Compared to L-enantiomeric peptides such as ziconotide, D-peptides are much more resistant (in vivo) to proteases and thus offer the possibility of oral administration with long elimination half-lives. Moreover, they are usually not or only minimally immunogenic.

A further embodiment relates to the above-described composition for use in administration of 1 µg to 1 g per kilo of body weight, preferably 100 µg to 10 mg/kg of body weight, and particularly preferably 0.5 to 5 mg/kg of body weight.

An embodiment relates to the above-described composition for enteral, intravenous, subcutaneous, intraperitoneal, intranasal or oral administration, preferably oral administration.

Advantageously, the above-described composition preferably has a $IC_{50}$ value of 1 nanomolar to 1 millimolar for N-type NCCs of 10 nM to 100 µM, particularly preferably 100 nM to 10 µM, and in particular 100 nM to 1 µM.

In a variant, the composition to be used according to the invention comprises or consists of peptides selected from the group consisting of or comprising:

ANK1; (free N-terminus, preferably amidated C-terminus): rkrirlvyhinr (SEQ ID NO: 8);
ANK2; (free N-terminus, preferably amidated C-terminus): rkrirl06yhinr (SEQ ID NO: 9);
ANK3; (free N-terminus, preferably amidated C-terminus): rkrirl06yhwnr (SEQ ID NO: 10);
ANK4; (free N-terminus, preferably amidated C-terminus): rkrirlvyhwnr (SEQ ID NO: 11);
ANK5; (free N-terminus, preferably amidated C-terminus): rkrvrlvyhkkr (SEQ ID NO: 12);
ANK6; (free N-terminus, preferably amidated C-terminus): rkrirlvtkkkr (SEQ ID NO: 13);
ANK7; (free N-terminus, preferably amidated C-terminus): rkrvrl02thikr (SEQ ID NO: 14);
ANK15; (free N-terminus, preferably amidated C-terminus): rprvrl06yhwnr (SEQ ID NO: 15);
ANK16; (free N-terminus, preferably amidated C-terminus): rkr7rlvtkrnr (SEQ ID NO: 16);
ANK17; (free N-terminus, preferably amidated C-terminus): rkrirl06yhikr (SEQ ID NO: 17);
ANK18; (free N-terminus, preferably amidated C-terminus): rpr07rlhtkkkr (SEQ ID NO: 18);

where 02: 4-fluorophenylalanine (D), 06: phenylglycine (D), 07: D-homoarginine.

In an alternative, the derivatives of the peptides to be used according to the invention and described above are cyclized or amidated peptides.

In a further embodiment, the peptides to be used according to the invention are linked by mutual covalent bonding of the free C-terminus to the free N-terminus and are accordingly in cyclized form. This ring closure is also advantageous in that the carboxyl group at the free C-terminus is no longer present. The peptides advantageously have an amino acid sequence in which cyclization of the linear molecule has taken place e.g. by means of covalent bonding of the first to the last amino acid, for example by means of a condensation reaction. Of course, there are further possibilities for cyclization, e.g. by means of linking of other amino acids to one another. Solely as an example, one can mention linkage of the second amino acid to the last amino acid. Any other possible linkage is also conceivable. In cases where the first and the last amino acid of the peptide are linked to each other, it is advantageous for there to be no open ends in the peptide chain (amino acid sequence). A further result of this measure is that all peptides with linear amino acid sequences yielding the same amino acid sequences after cyclization that can no longer be distinguished from one another are in this sense identical.

Example: The linear amino acid sequence of the known peptide D3 is rprtrlhthrnr (SEQ ID NO: 2). The corresponding cyclized peptide, "cD3," which is linked by an amide bond between the N-terminal amino group and the C-terminal carboxyl, can no longer be distinguished from the cyclized peptides of the sequence prtrlhthrnrr, rtrlhthrnrrp, trlhthrnrrpr, rlhthrnrrprt, lhthrnrrprtr, hthrnrrprtrl, thrnrrprtrlh, hrnrrprtrlht, rnrrprtrlhth, nrrprtrlhthr, or rrprtrlhthrn. In addition, cD3 can further be derived from each of these sequences.

The situation is similar for RD2: ptlhthnrrrrr (SEQ ID NO: 1), with the cyclized peptides of the sequence tlhthnrrrrrp, lhthnrrrrrpt, hthnrrrrrptl, thnrrrrrptlh, hnrrrrrptlht, nrrrrrptlhth, rrrrrptlhthn, rrrrptlhthnr, rrrptlhthnrr, rrptlhthnrrr, rptlhthnrrrr and the designation "cRD2".

The production of cyclized peptides belongs to the prior art, and can for example be carried out according to the method described in DE 10 2005049537 A1.

Advantageously, the result of cyclization via the first and last amino acid of the peptide is that there are no longer any "open" ends of the peptide chain, which are often attack points for peptide-degrading activities in cells, animals, or humans, e.g. by aminopeptidases and carboxypeptidases.

In a further embodiment of the invention, the peptides to be used according to the invention are amidated at the free C-terminus, therefore having an acid amide group instead of the carboxyl group. Instead of the carboxyl group (—COOH group), therefore, an acid amide group (—CONH2 group) is arranged at the C-terminus. The peptide is advantageously amidated at the free C-terminus. This allows the further object to be particularly advantageously achieved in that a peptide not having a negative excess charge is provided that can bind to the target molecule with greater affinity and can be obtained in a simple manner.

Instead of the carboxyl group, in an alternative of the invention, one has a group composed of: COH, COCl, COBr, a CONH-alkyl radical, and a CONH-alkyl-amine radical (positive net charge), wherein the invention is not limited thereto.

Moreover, in an embodiment, each of the peptides to be used according to the invention is lengthened or shortened by one or two amino acids at the N-terminus and/or the C-terminus with respect to the original sequence. In an alternative, one terminus has one or two additional amino acids, while the other terminus has one or two fewer amino acids. The peptides are preferably lengthened with respect to the original sequence at the C-terminus by one amino acid selected from the group of amino acids rlht, preferably r.

Preferred derivatives are cyclized (cycl-) peptides, amidated peptides and/or peptide sequences lengthened by one amino acid, preferably arginine r, at the C-terminus, in particular D3r rprtrlhthrnrr (SEQ ID NO: 5), and cyclized D3r. Further preferred derivatives are cyclized RD2 and the respective linear amidated forms thereof and/or the peptide sequence RD2r ptlhthnrrrrrr (SEQ ID NO: 19), lengthened by one amino acid, preferably arginine r, at the C-terminus.

Further subject matter of the present invention is therefore also the peptide RD2r ptlhthnrrrrr (SEQ ID NO: 19), a 13-mer based on RD2 which is extended by one amino acid at the C-terminus, preferably r. The amidated and/or cyclized form cRD2r (analogous to cRD2) is also subject matter of the invention. Further subject matter of the invention is the peptide RD2r and thus also the amidated and/or cyclized form, preferably cRD2r, for use in medicine or as a medicinal product, preferably for use in the treatment of pain or in therapy for pain, in particular chronic and neuropathic pain. Further peptides to be used according to the invention are: RD2RD2, ptlhthnrrrrrrptlhthnrrrrr (SEQ ID NO: 3), RD2D3 ptlhthnrrrrrprtrlhthrnr (SEQ ID NO: 4), cycl-RD2RD2, ptlhthnrrrrrptlhthnrrrrr (SEQ ID NO: 20), cycl-D3r, rprtrlhthrnrr (SEQ ID NO: 21), D3p, rprtrlhthrnrp (SEQ ID NO: 6) and cycl-D3p and also D3a, rprtrlhthrnra (SEQ ID NO: 7) and cycl-D3a.

"Homologous sequences" or "homologs" signifies within the meaning of the invention that an amino acid sequence has an identity with one of the above-mentioned amino acid sequences of the monomers of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. In addition to the term "identity," the terms "homolog" or "homology" are used in the present description with the same meaning. The identity between two nucleic acid sequences or polypeptide sequences is calculated by conducting a comparison using the program BESTFIT based on the algorithm of Smith, T. F. and Waterman, M. S (Adv. Appl. Math. 2: 482-489 (1981)), setting the following parameters for amino acids: gap creation penalty: 8 and gap extension penalty: 2; and the following parameters for nucleic acids: gap creation penalty: 50 and gap extension penalty: 3. Preferably, the identity between two nucleic acid sequences or polypeptide sequences is defined by the identity of the nucleic acid sequence/polypeptide sequence over the respective entire sequence length, as in calculation by comparison using the program GAP based on the algorithm of Needleman, S. B. and Wunsch, C. D. (J. Mol. Biol. 48: 443-453), setting the following parameters for amino acids: gap creation penalty: 8 and gap extension penalty: 2; and the following parameters for nucleic acids gap creation penalty: 50 and gap extension penalty: 3.

Within the meaning of the present invention, two amino acid sequences are identical when they possess the same amino acid sequence.

In an alternative, homology or identity is determined by the respective total length of the corresponding peptides. In another alternative, comparison and thus determination of identity or homology takes place solely via partial regions.

In this alternative as well, the polypeptides to be used according to the invention have a homology of at least 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In a further embodiment of the invention, the composition comprises or consists of polymers comprising or consisting of RD2 (SEQ ID NO: 1), D3 (SEQ ID NO: 2), homologs having at least 50% identity and derivatives of RD2 (SEQ ID NO: 1) and D3 (SEQ ID NO: 2) or the further peptides described above. The polymer to be used according to the invention comprises 2, 3, 4, 5, 6, 7, 8, 9, 10 or more of the above-described monomeric peptides.

Dimers selected from the group consisting of or comprising RD2D3 (SEQ ID NO: 1) (SEQ ID NO: 2), D3RD2 (SEQ ID NO: 2) (SEQ ID NO: 1), D3D3 (SEQ ID NO: 2) (SEQ ID NO: 2) and RD2RD2 (SEQ ID NO: 1) (SEQ ID NO: 1) or homologs or derivatives are preferably used.

Any desired combination of 2, 3, 4, 5, 6, 7, 8, 9, 10 or more of the above-described sequences in linear or cyclized form can form the polymer.

Polymers can be produced for example by chemical synthesis or peptide synthesis.

In a variant of the present invention, the peptides can be linked to one another in linear fashion, in particular as described above. In another variant, the peptides are linked to one another in branched fashion to form the polymer according to the invention. According to the invention, a branched polymer can be a dendrimer in which the monomers are linked to one another by covalent or non-covalent bonding. Alternatively, the peptides can also be linked to a platform molecule (such as e.g. PEG or sugar) and thus form a branched polymer.

The monomeric peptides are linked in linear fashion head to head, tail to tail or head to tail, with or without additional linkers, and in an alternative, are cyclized by overall covalent linkage, with or without additional linkers (e.g. one or a plurality of amino acids), of the two remaining ends.

In an embodiment of the present invention, the peptides to be used according to the invention are covalently linked to further amino acids, linkers, spacers and/or functional groups.

In an alternative of the present invention, the properties of the peptide are not modified by these further amino acids, linkers, spacers and/or functional groups. In a further alternative, the further amino acids, linkers, spacers and/or functional groups cause a change in the properties of the peptide. In such an embodiment, the selectivity and/or affinity of the polymers according to the invention with respect to the N-type NCCs is enhanced.

A linker is understood to be one or a plurality of molecules that are bonded to the peptides by covalent bonds, wherein these linkers can also be bonded to one another by covalent bonds.

Functional groups are understood to be molecules covalently bonded to the peptides. In a variant, the functional groups comprise biotin groups. This allows strong covalent bonding to streptavidin.

In an embodiment of the present invention, the peptides comprise so-called spacers. A spacer is understood to be a molecule that is bonded to the peptide via covalent bonds and possesses specified physical and/or chemical properties by means of which the properties of the peptide are modified. In an embodiment, hydrophilic or hydrophobic, preferably hydrophilic spacers, are used. Hydrophilic spacers are selected from the group of molecules comprising polyethylene glycol, sugar, glycerol, poly-L-lysine or beta-alanine.

In an alternative, the peptides are linked to a further substance.

In a variant, these substances are drugs or active compounds defined according to the German Drug Law § 2 or § 4 (19), as of September 2012. In an alternative, active compounds are therapeutically active substances that are used as medicinally active substances.

In another variant, the substances are carriers for controlled release of the active compound (also referred to as drug carrier systems), whose purpose, on the one hand, is to prevent rapid excretion of active compounds from the body. Most conventional active compounds are small and therefore remain in the bloodstream for only a short period, as their small size means that they are below the renal threshold and are therefore separated from the blood and excreted. On the other hand, these carrier systems specifically transport the active compounds to the vicinity of specified organs or cells and release them there in a controlled manner.

In a further variant, the substances are compounds that enhance the action of the peptides. In an alternative, such compounds are aminopyrazole and/or aminopyrazole derivatives. Within the meaning of the invention, aminopyrazole derivatives are 3-aminopyrazole-5-carboxylic acid or 3-nitropyrazole-5-carboxylic acid, as well as all derivatives in which the heterocyclic CH group is substituted by —CR— or —N— or —O— or —S—, and also all peptide dimers, trimers, or tetramers derived therefrom, preferably aminopyrazole trimers. In a further alternative, these are compounds that improve the solubility of the peptides and/or their passage through the blood-brain barrier.

The substance is linked to the peptide, wherein the linkage is a covalent bond or is not a covalent bond. Linkage takes place here via hydrogen bonds, hydrophilic, hydrophobic, or electrostatic interaction or bonding and/or steric immobilization.

Further subject matter of the present invention is a method for reducing the release of neurotransmitters compared to a control, characterized in that a composition consisting of or comprising peptides selected from the group consisting of or comprising RD2 (SEQ ID NO: 1), D3 (SEQ ID NO: 2), homologs having at least 50% identity and derivatives of RD2 (SEQ ID NO: 1) or D3 (SEQ ID NO: 2) and also polymers comprising or consisting of RD2 (SEQ ID NO: 1), D3 (SEQ ID NO: 2), homologs having at least 50% identity and derivatives of RD2 (SEQ ID NO: 1) and under D3 (SEQ ID NO: 2) for use as an analgesic is brought into contact with the N-type NCCs.

In particular, the calcium influx through an NCC compared to a control is reduced by means of the method according to the invention.

Further subject matter of the invention is also a method for inhibiting an N-type NCC compared to a control characterized in that the latter is brought into contact with a composition consisting of or comprising peptides selected from the group consisting of or comprising RD2 (SEQ ID NO: 1), D3 (SEQ ID NO: 2), homologs having at least 50% identity and derivatives of RD2 (SEQ ID NO: 1) or D3 (SEQ ID NO: 2) and also polymers comprising RD2 (SEQ ID NO: 1), D3 (SEQ ID NO: 2), homologs having at least 50% identity and derivatives of RD2 (SEQ ID NO: 1) and/or D3 (SEQ ID NO: 2).

Within the meaning of the invention, the phrase "bringing into contact" means that conditions are present that allow an interaction between the peptides to be used according to the invention and the N-type NCC, in particular physical and/or chemical interactions, such as e.g. the formation of coordination bonds or hydrogen bonds.

The selection of a control is a routine part of an experimental approach. One uses as a control an organism that in an alternative is identical to the organism to be investigated. The organism to be investigated is treated with the composition according to the invention or brought into contact therewith in the broadest sense of the term, while the control is not subjected to this procedure. According to the invention, the term organism also includes parts of organisms, tissues, tissue samples, individual cells or cell cultures, parts of cells such as membrane-comprising NCCs, preferably of the N-type or L-type, or neuronal calcium channels comprising artificial membranes such as e.g. a double lipid membrane, preferably of the N-type and/or L-type. Both the control and the organism to be investigated are selected from the above list. In another alternative, the control is defined according to the specifications of the clinical studies.

Within the meaning of the invention, inhibition refers to a reduction in the activity of neuronal calcium channels, preferably of the N type, by the composition to be used according to the invention compared to a control. According to the invention, the control is not brought into contact with the composition. As an alternative to this, the control can also be brought into contact with known inhibitors.

Based on a comparison of the use of known inhibitors with the use of the composition to be used according to the invention, the person having ordinary skill in the art can also seek to draw conclusions as to the efficacy of the composition according to the invention.

In an embodiment of the present invention, inhibition is determined at a concentration equivalent or equal to the $IC_{50}$ value.

The compositions to be used according to the invention inhibit N-type NCCs to at least 10%, 15%, 20%, 25%, preferably 30%, particularly preferably 40%, 50%, 60%, 70%, 80%, and in particular 90% or 100%.

In an embodiment, inhibition is determined according to the invention by means of the so-called patch clamp technique. In this technique, the ion current passing through the calcium channel is measured at different voltages. Inhibition of the neuronal calcium channel is therefore determined based on the reduction in the ion current. In an alternative, the ion current is reduced by at least 10%, 15%, 20%, 25%, preferably 30%, 35%, particularly preferably 40, 42, 44, 46, 48, 50%, 52, 54, 56, 58, 60%, 70%, 80%, and in particular 90% or 100%. Preferably, the reduction is determined at a peptide concentration equal to the $IC_{50}$ value. In an embodiment, the patch clamp measurement is determined by bringing the corresponding channel into contact with the composition to be used according to the invention at a concentration of 150 nM.

The methods according to the invention are characterized in that the function of L-type NCCs is not modified compared to a control. In other words, the calcium influx through the L-type NCCs is not modified compared to a control. The peptides to be used according to the invention act specifically and/or selectively on N-type NCCs.

Further subject matter of the present invention is also use of the peptides to be used according to the invention as a substitute for conotoxin.

In this manner, brining into contact of the NCCs or membranes comprising NCCs, or the corresponding sources comprising NCCs, can be carried out in vitro (ex vivo).

The invention also relates to the treatment of chronic and/or neuropathic pain, i.e. treatment for pain relief, in which the individual to be treated is administered the peptides to be used according to the invention by enteral, intravenous, subcutaneous, intraperitoneal, intranasal or oral administration, preferably oral administration, in a concentration von 1 µg to 1 g/kg of body weight.

The invention thus also relates to a method in which the peptides to be used according to the invention are incorporated into pharmaceutical formulations by means of conventional methods known to the person having ordinary skill in the art. Subject matter of the invention is therefore also the use of the above-described peptides in pharmaceutical formulations. A pharmaceutical formulation comprising the peptides according to the invention described above is therefore also subject matter of the present invention.

Moreover, further subject matter of the present invention is the use of a composition according to claim 1 for the production of an analgesic, a drug for use in pain therapy and/or a drug for the treatment of chronic and neuropathic pain.

Further subject matter of the invention is the use of a composition according to claim 1 for inhibiting N-type neuronal calcium channels NCCs.

In the method according to the invention, the further peptides, derivatives and homologs described above can also be used.

BRIEF DESCRIPTION OF THE DRAWINGS

In the accompanying drawings.

DETAILED DESCRIPTION OF EMBODIMENTS OF THE INVENTION

The further examples can be carried out with any of the above-described peptides.

EXAMPLES

1. RD2 (SEQ ID NO: 1) (C-terminal amidated)
A. Protein Constructs:

The coding regions of the two different alpha1 pore-forming units (CaValpha1) of the voltage-dependent calcium channel were fused in frame (C-terminal fusion) with the fluorescent proteins as follows: the unit of rabbit CaV1.2 (UniProtKB: P15381) was fused with YFP (CaV1.2-YFP), while the human unit CaV2.2 (UniProtKB: Q00975-1) was fused with GFP (CaV2.2-GFP). The beta-subunit CaVbeta2e (UniProtKB: Q8VGC3-2) was linked to mRFP (CaVbeta2e-mRFP), and CaVbeta4 (UniProtKB: O00305.2) was linked to mCherry (CaVbeta4-mCherry).

B: Cell Transfection:

As the normal function and surface expression of the CaValpha1 subunit requires association with the CaVbeta subunit, tsA201 cells were transiently co-transfected with either CaV1.2-YFP and CaVbeta2e-mRFP or CaV2.2-GFP and CaVbeta4-mCherry. The transfection was carried out using Lipofectamine 2000™ (Invitrogen), and the successfully transfected cells were identified by means of fluorescent signals. Electrophysiological discharges were carried out 24-48 hours after transfection.

C. Electrophysiology:

Ion currents were measured using the whole cell patch clamp technique with an EPC-10 amplifier with implemented PatchMaster software (HEKA Elektronik). Barium was used as a carrier. Borosilicate glass pipettes with resistance values of 0.9-2 MΩ were pulled on a Sutter P-1000 puller (Harvard Apparatus), and their tips were subjected to surface heat-polishing using a Narishige MF-830 microforge. External measuring solution used: 140 mM TEA-MeSO$_3$, 10 mM BaCl$_2$, and 10 mM HEPES (pH 7.3); internal measuring solution used: 135 mM Cs-MeSO$_3$, 10 mM EGTA, 5 mM CsCl$_2$, 1 mM MgCl$_2$, 4 mM MgATP, 0.4 mM Na2GTP and 10 mM HEPES (pH 7.3). Data analysis was carried out using a combination of the software Fit-Master (HEKA), Origin (OriginLab) and Excel (Microsoft). All data are shown as mean values±SEM. Ion currents were corrected using the P/4 protocol (leak subtraction).

In order to investigate the pharmacological effect of RD2 (SEQ ID NO: 1), cells were detached and transferred to a perfusion flow that either contained or did not contain the test substance. The observations were conducted under constant perfusion in order to ensure a constant concentration of the test substance. RD2 (SEQ ID NO: 1) was dissolved in DMSO with a final concentration of 1 mM and dissolved in the external measuring solution to 150 nM shortly before use. Control experiments were conducted with the known CaV1.2 and CaV2.2 calcium channel blockers nimodipine (10 µM) and omega-conotoxin (1 nM).

Figure 1A:
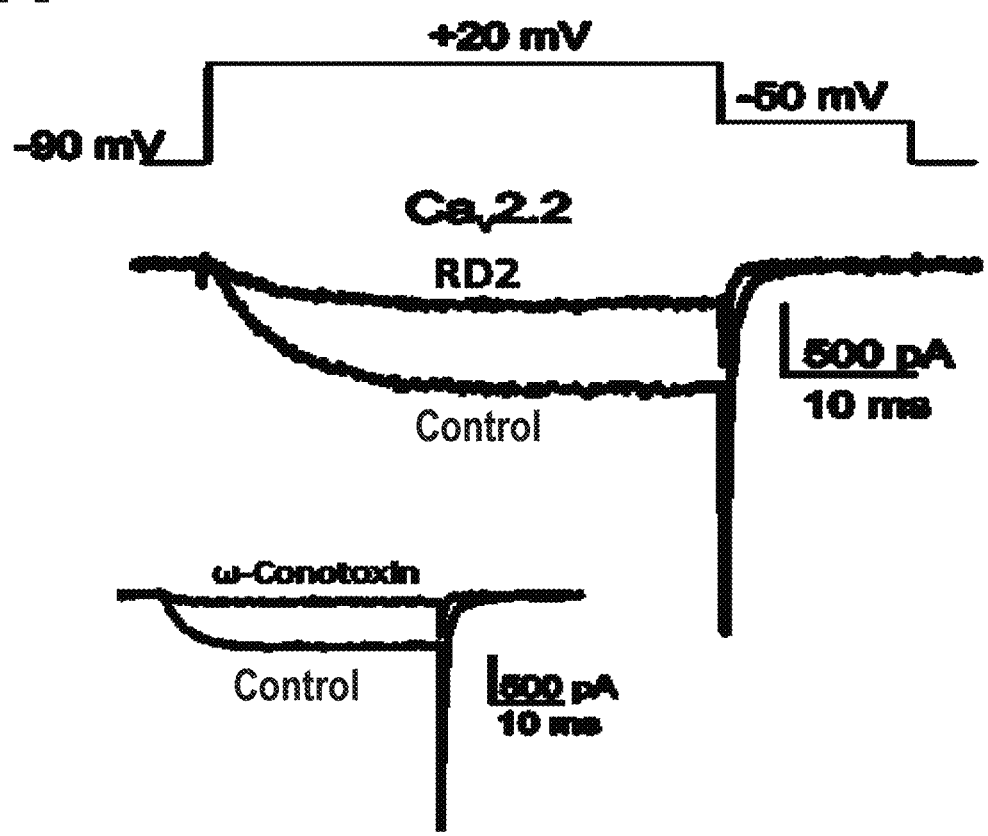
FIG. 1A is a representative graph of current intensity mediated by a CaV2.2 channel as set forth in Example 1 below.
Figure 1B:
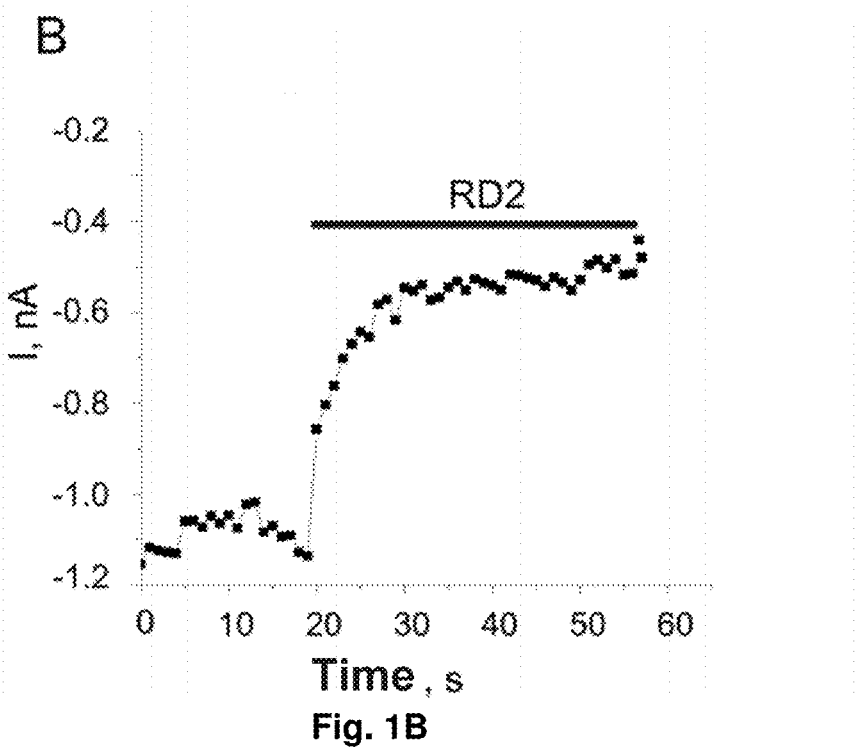
FIG. 1B is a graph representing a course over time of inhibition, taken in a representative cell, as set forth in Example 1 below.
Figure 1C:
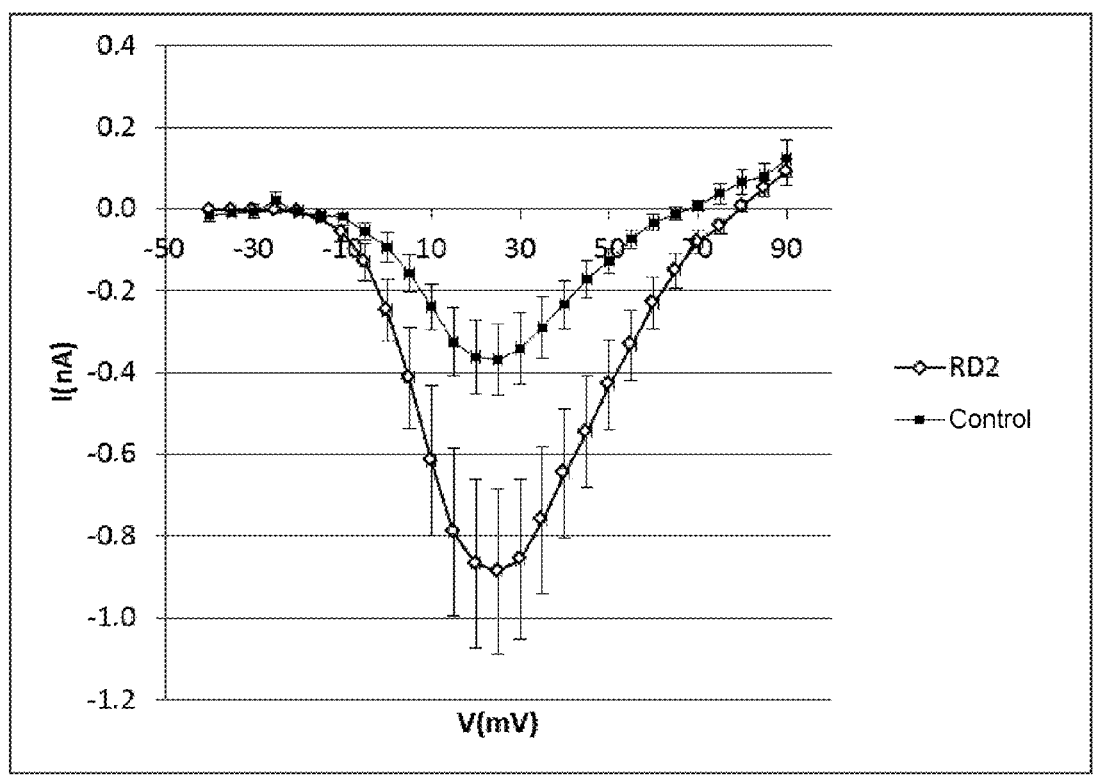
FIG. 1C represents the average ratio of current intensity to voltage of cells that express CaV2.2 in the presence and absence of RD2 as set forth in Example 1 below.
Figure 1D:
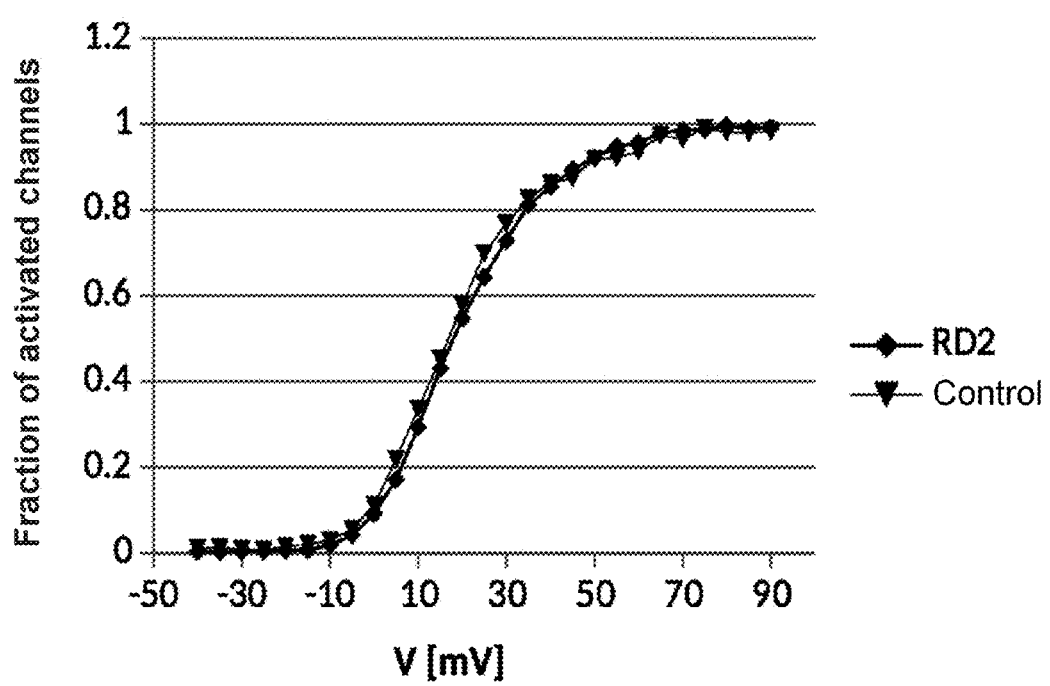
FIG. 1D shows the fraction of activated channels vs. the voltage plot for the same cells as in FIG. 1C as set forth in Example 1 below.

D. Results:

Effect of RD2 (SEQ ID NO: 1) on CaV2.2-mediated ion currents:

CaV2.2 is localized in the presynaptic nerve endings and mediates neurotransmission in central synapses. CaV2.2-mediated ion currents were taken up by tsA201 cells that express CaV2.2/CaVbeta4. Perfusion of the cells with an external measuring solution comprising RD2 (SEQ ID NO: 1) (150 nM), but not with the external measuring solution alone, resulted in a significant reduction in the ion current (FIG. 1A, B; where A: Representative graph of current intensity mediated by a CaV 2.2 channel, produced during a pulse of 40 MS, based on a holding potential of −90 mV to +20 mV before and after contact with composition comprising 150 mM of RD2 (SEQ ID NO: 1); B: Course over time of inhibition, taken in a representative cell, during successive pulses of −90 mV to +20 mV, every five seconds). The current-to-voltage plot (I-V) showed a reduction in the ion current at all tested voltages of up to 55% (FIG. 1C: Average ratio of current intensity to voltage of cells that express CaV 2.2 in the presence and absence of RD2 (SEQ ID NO: 1) (n=7)). As a blockade of the ion current was not accompanied by a change in voltage-dependent activation of the channel, a pore-blocking mechanism of RD2 (SEQ ID NO: is assumed (FIG. 1D: Fraction of activated channels vs. the voltage plot (activation curve) for the same cells as in FIG. C.; as a control; there is therefore no change in the function or mechanism of the channel, as the curves are on top of each other and not displaced). Ion currents are interrupted after administration of 1 nM of the CaV2.2 blocker omega-conotoxin, which confirms that they were mediated via the CaV2.2 channel. (FIG. 1A insert).

Figure 2A:
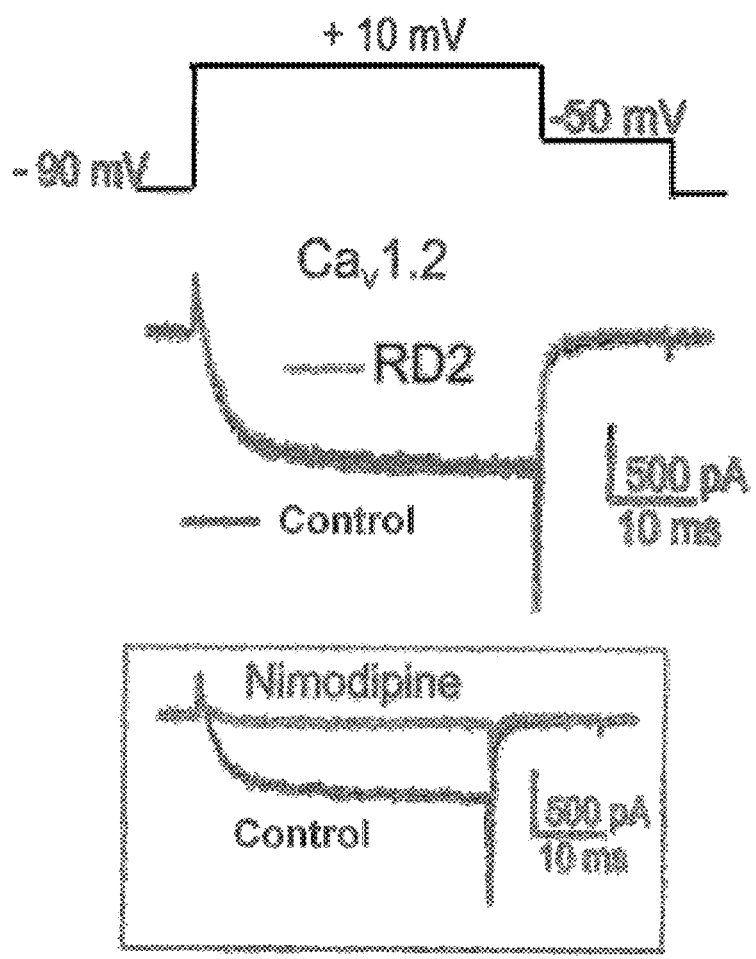
FIG. 2A is a representative image of current intensity mediated by a CaV1.2 channel as set forth in Example 1 below.
Figure 2B:
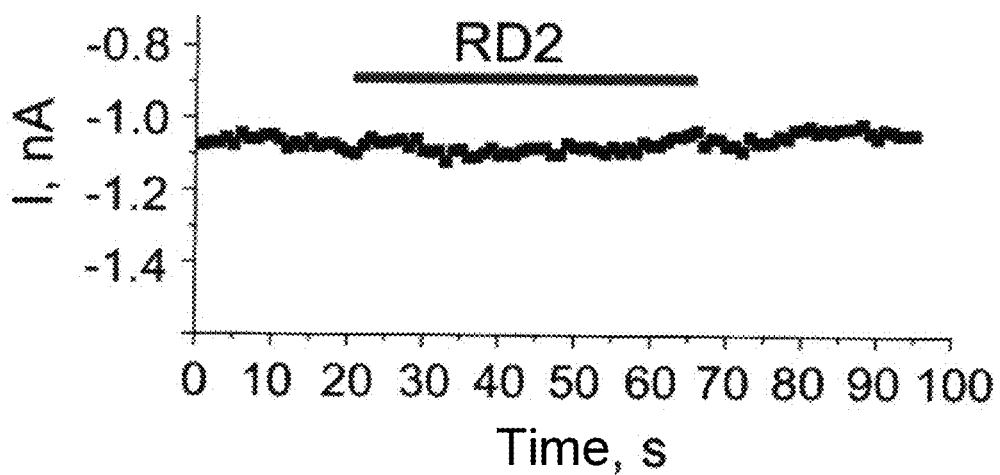
FIG. 2B represents the change in current intensity on perfusion with several substances as set forth in Example 1 below.
Figure 2C:
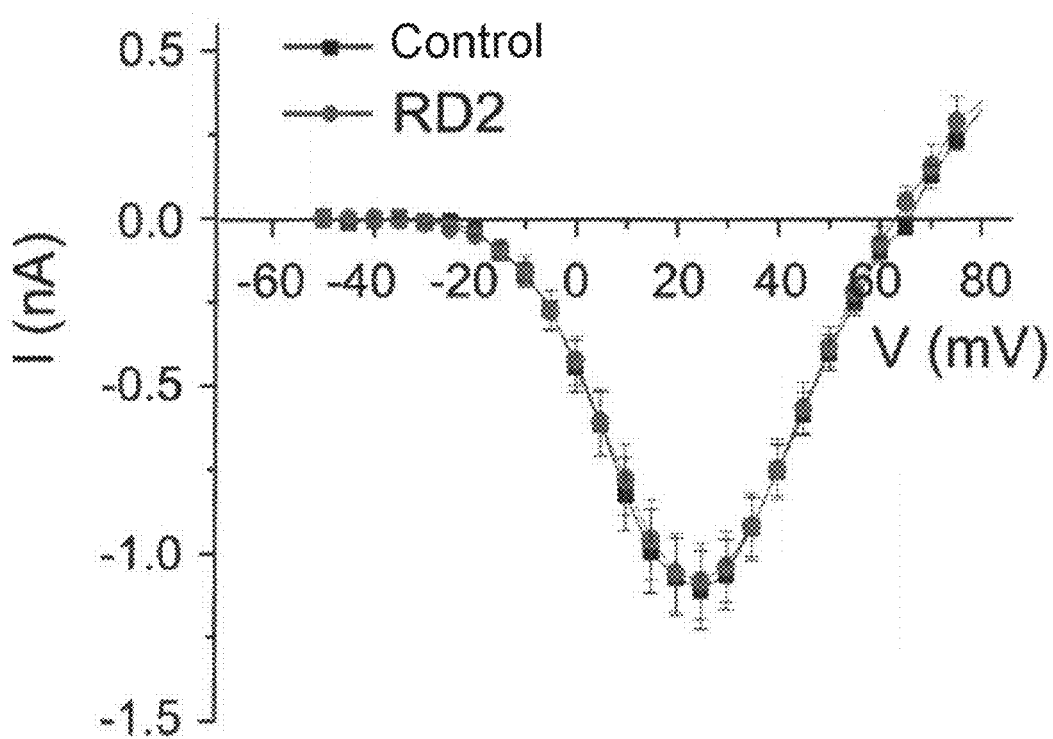
FIG. 2C represents the average ratio of current intensity to voltage of cells that express CaV1.2 in the presence and absence of RD2 as set forth in Example 1 below.
Figure 2D:
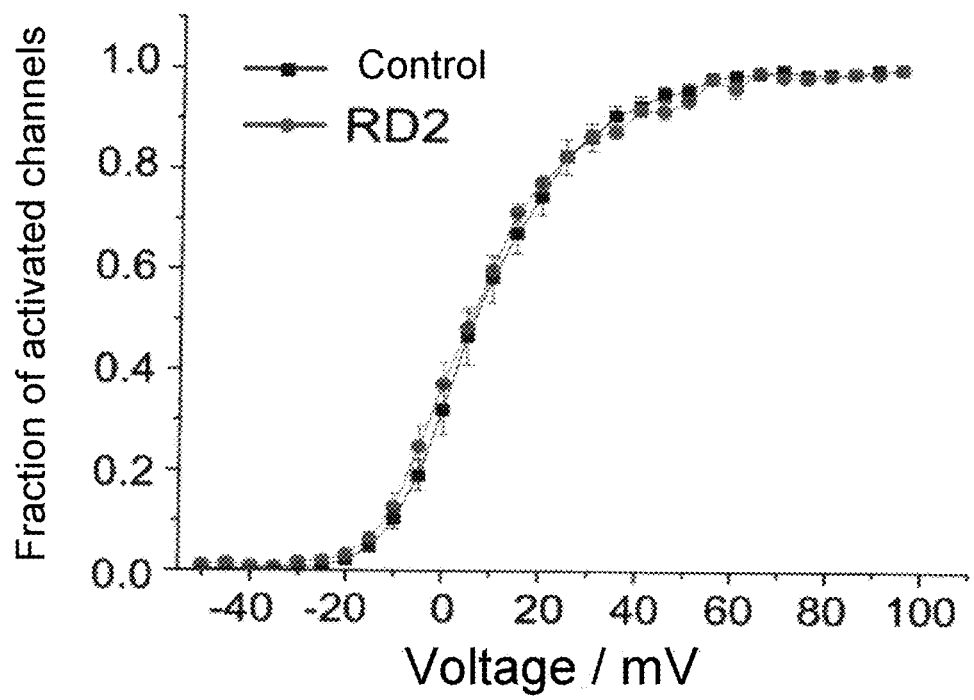
FIG. 2D shows the fraction of activated channels vs. the voltage plot for the same cells as in FIG. 2C as set forth in Example 1 below.

Effect of RD2 (SEQ ID NO: 1) on CaV1.2-mediated ion currents:

CaV1.2 is the L-type calcium channel primarily expressed in the heart and responsible for coupling of the electrical activation of the cardiomyocytes with the myofilament contraction. The ion currents were taken up by CaV1.2 and CaVbeta2e co-expressing cells and remained virtually unchanged after exposure to 150 nM of RD2 (SEQ ID NO: 1) (FIG. 2A: Representative image of current intensity mediated by a CaV 1.2 channel, produced during a pulse of 40 ms, based on a holding potential of −90 mV to +10 mV before and after contact with a composition comprising 150 mM of RD2 (SEQ ID NO: 1). FIG. 2B: No change in current intensity on perfusion with 150 nM of RD2 (SEQ ID NO: 1)). In contrast, perfusion with 10 µM of nimodipine, a known blocker of the CaV1.2 channel, led to almost complete blockade of the ion current. The voltage dependency of activation of the CaV1.2 channel was therefore not affected by the presence of RD2 (SEQ ID NO: 1) (FIGS. 2C and 2D).

E: Conclusion

Figure 3:
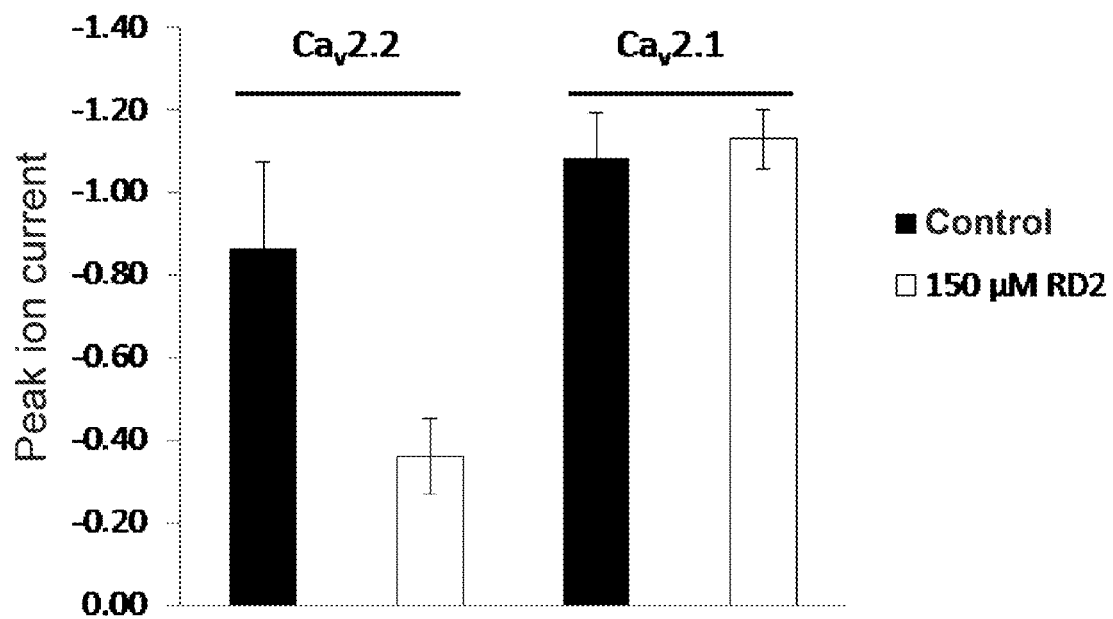
FIG. 3 represents the capacity of RD2 to block ion currents mediated via the CaV2.2 and CaV1.2 channels as set forth in Example 1 below.

RD2 (SEQ ID NO: 1) was tested at a concentration of 150 nM for its capacity to block ion currents mediated via the CaV2.2 and CaV1.2 channel. The tests were conducted in CaV2.2 and CaV1.2 channel-expressing tsA201 cells using the whole cell patch clamp technique. RD2 (SEQ ID NO: 1) blocks the CaV2.2 channel, while the CaV1.2 channel is insensitive to RD2 (SEQ ID NO: 1) in the tested concentration (FIG. 3).

2. D3 (SEQ ID NO: 2) (C-terminal amidated)

A. Protein Constructs:

The coding region of the human alpha1 pore-forming units (CaValpha1) of the voltage-dependent calcium channel CaV2.2 (UniProtKB: Q00975-1) was fused with GFP to form CaV2.2-GFP. The beta-subunit CaVbeta4 (UniProtKB: 000305.2) was fused with mCherry to form CaVbeta4-mCherry.

B: Cell Transfection:

As the normal function and surface expression of the CaValpha1 subunit requires association with the CaVbeta subunit, tsA201 cells were transiently co-transfected with CaV2.2-GFP and CaVbeta4-mCherry. The transfection was carried out using Lipofectamine 2000™ (Invitrogen), and the successfully transfected cells were identified by means of fluorescent signals. Electrophysiological discharges were carried out 24-48 hours after transfection.

C. Electrophysiology:

Ion currents were measured using the whole cell patch clamp technique with an EPC-10 amplifier with implemented PatchMaster software (HEKA Elektronik). Barium was used as a carrier. Borosilicate glass pipettes with resistance values of 0.9-2 MC were pulled on a Sutter P-1000 puller (Harvard Apparatus), and their tips were subjected to surface heat-polishing using a Narishige MF-830 microforge. External measuring solution used: 140 mM TEA-MeSO$_3$, 10 mM BaCl$_2$, and 10 mM HEPES (pH 7.3); internal measuring solution used: 135 mM Cs-MeSO$_3$, 10 mM EGTA, 5 mM CsCl$_2$, 1 mM MgCl$_2$, 4 mM MgATP, 0.4 mM Na2GTP and 10 mM HEPES (pH 7.3). Data analysis was carried out using a combination of the software Fit-Master (HEKA), Origin (OriginLab) and Excel (Microsoft). All data are shown as mean values±SEM. Ion currents were corrected using the P/4 protocol (leak subtraction).

In order to investigate the pharmacological effect of D3 (SEQ ID NO: 2), cells were detached and transferred to a perfusion flow that either contained or did not contain the test substance. The observations were conducted under constant perfusion in order to ensure a constant concentration of the test substance. D3 (SEQ ID NO: 2) was dissolved in DMSO with a final concentration of 1 mM and dissolved in the external measuring solution to 150 nM shortly before use. Control experiments were conducted with the known CaV2.2 calcium channel blocker omega-conotoxin (1 nM).

Figure 4A:
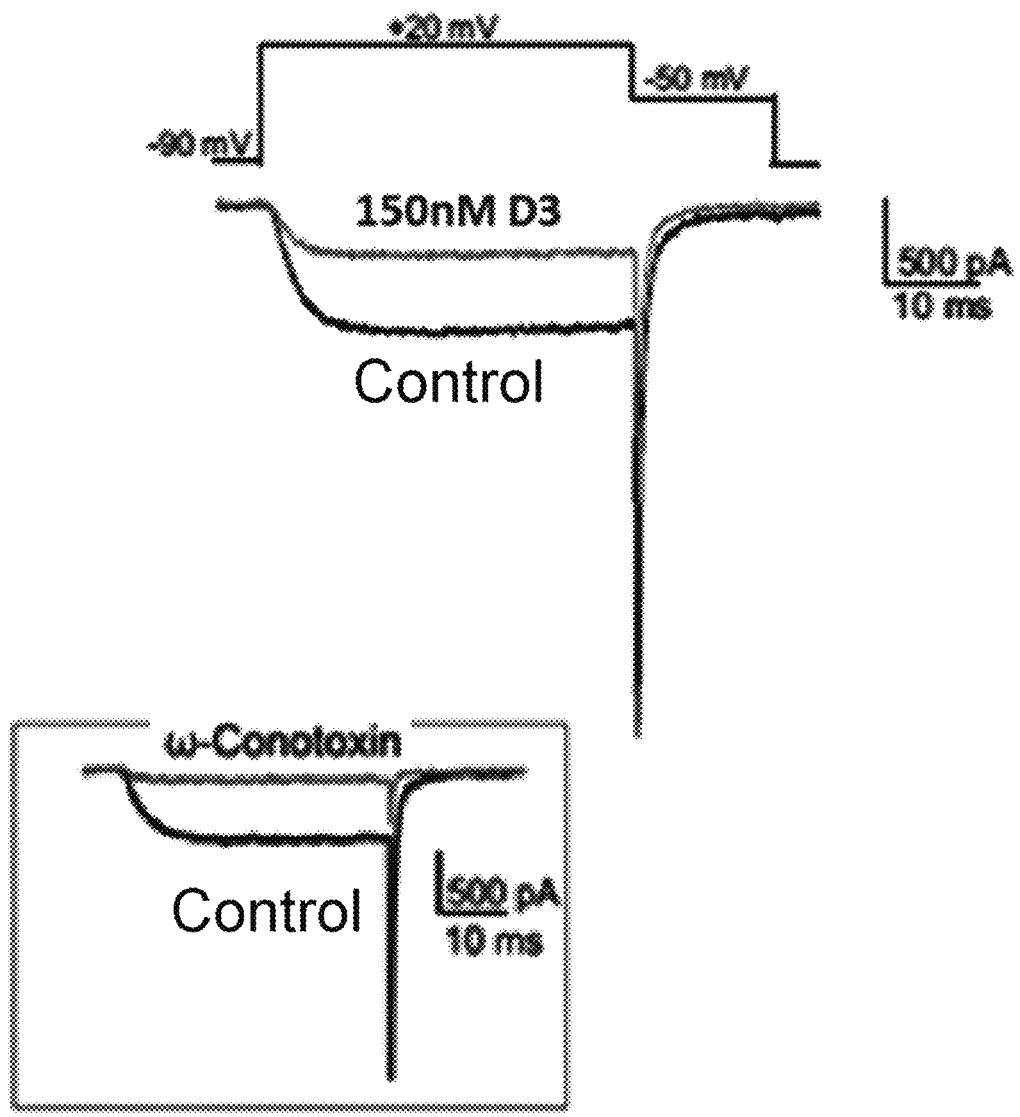
FIG. 4A is a representative image of current intensity mediated by a CaV2.2 channel as set forth in Example 2 below.
Figure 4B:
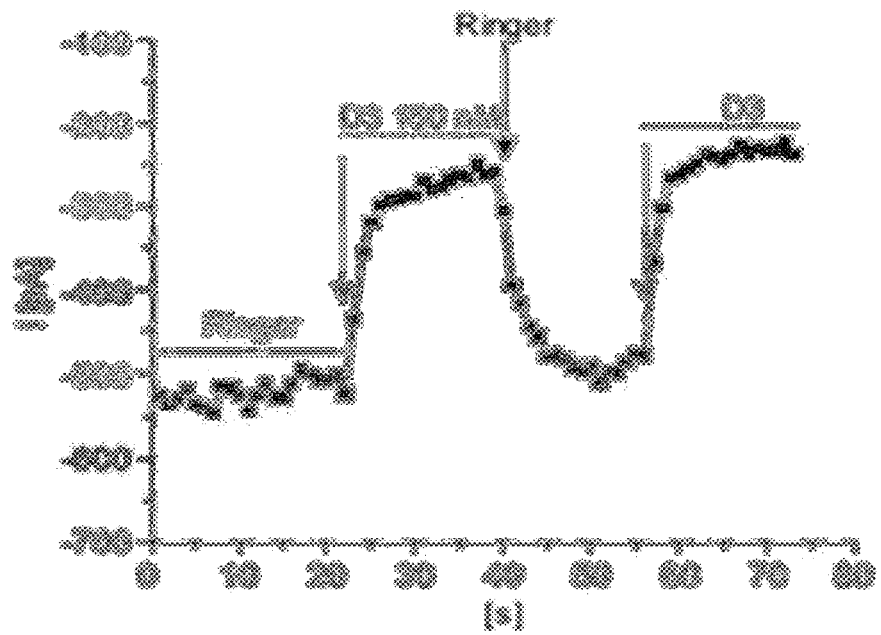
FIG. 4B shows the inhibition induced by D3 after perfusion with Ringer's solution as set forth in Example 2 below.
Figure 4C:
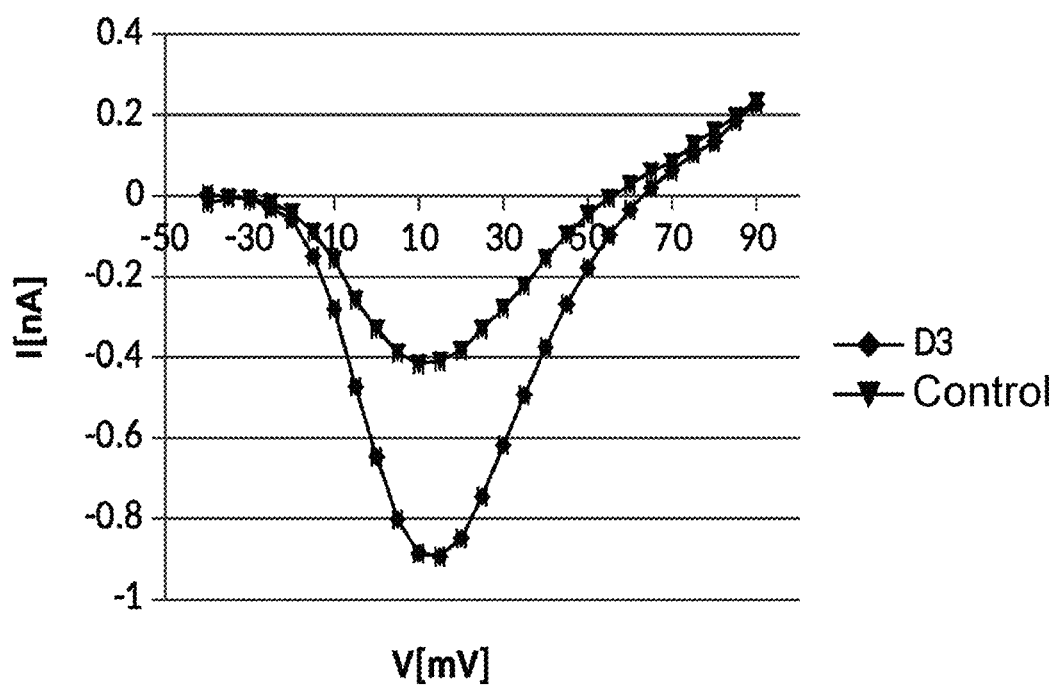
FIG. 4C shows a current to voltage plot for D3 with respect to CaV2.2 mediated ion currents as set forth in Example 2 below.
Figure 4D:
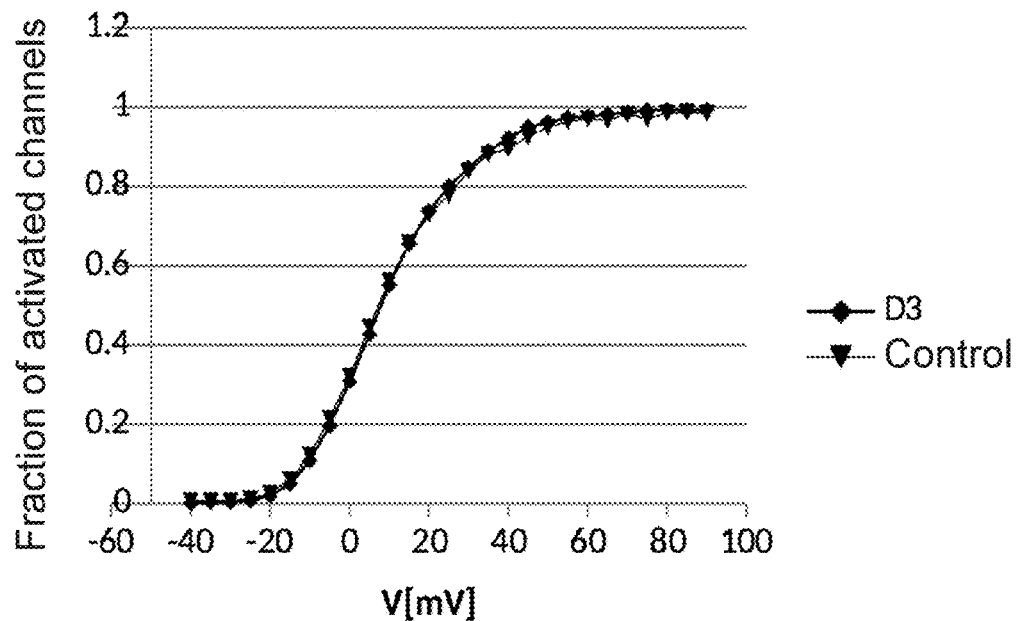
FIG. 4D shows the fraction of activated channels vs. the voltage plot for the same cells as in FIG. 4C as set forth in Example 2 below.

D. Results:

Effect of D3 (SEQ ID NO: 2) on CaV2.2-mediated ion currents:

CaV2.2-mediated ion currents were taken up by tsA201 cells that express CaV2.2/CaVbeta4. Perfusion of the cells with an external measuring solution comprising D3 (SEQ ID NO: 2) (150 nM), but not with the external measuring solution alone, resulted in a significant reduction in the ion current (FIG. 4A, B; where A: Representative image of current intensity mediated by a CaV 2.2 channel produced during a pulse of 40 ms, based on a holding potential of −90 mV to +20 mV before and after contact with a composition comprising 150 mM of D3 (SEQ ID NO: 2); 4B: The inhibition induced by D3 (SEQ ID NO: 2) is reversible after reperfusion with an external Ringer's solution. The current intensity was recorded during successive pulses of −90 mV+20 mV, every 5 sec.). The current-to-voltage plot (I-V) showed a reduction in the ion current at all tested voltages of up to 54% (FIG. 4C). As a blockade of the ion current was not accompanied by a change in voltage-dependent activation of the channel, a pore-blocking mechanism of D3 (SEQ ID NO: 2) is assumed (FIG. 4D). Ion currents are interrupted after administration of 1 nM of the CaV2.2 blocker omega-conotoxin, which confirms that they were mediated via the CaV2.2 channel (FIG. 4A, insert).

E: Conclusion

Figure 5:
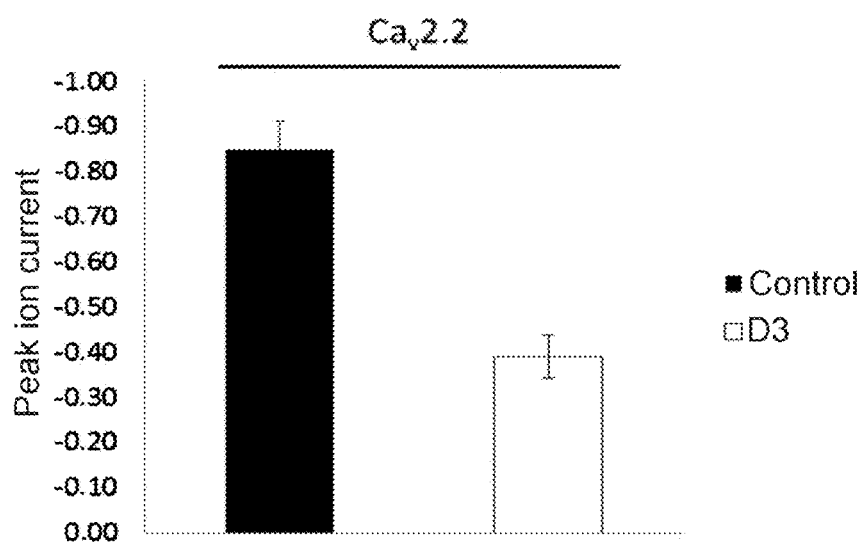
FIG. 5 represents the capacity of D3 to block ion currents mediated via the CaV2.2 channel a set forth in Example 2 below.

D3 (SEQ ID NO: 2) blocks the CaV2.2 channel (FIG. 5).

3. cD3 (cyclized D3 (SEQ ID NO: 2)) and cRD2 (cyclized RD2 (SEQ ID NO: 1))

The experiments were carried out analogously to examples 1 and 2.

Figure 6:
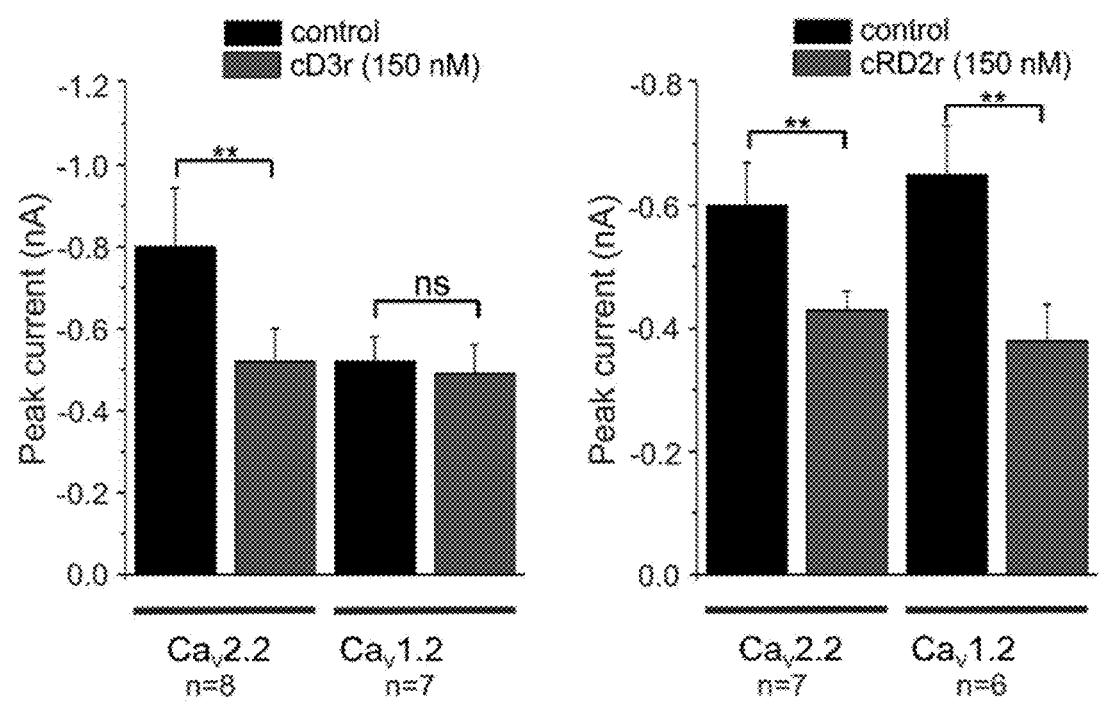
FIG. 6 represents the capacity of cD3 and cRD2 to block ion currents mediated via the CaV1.2 and CaV2.2 channels a set forth in Example 3 below.
Figures 7A, 7B:
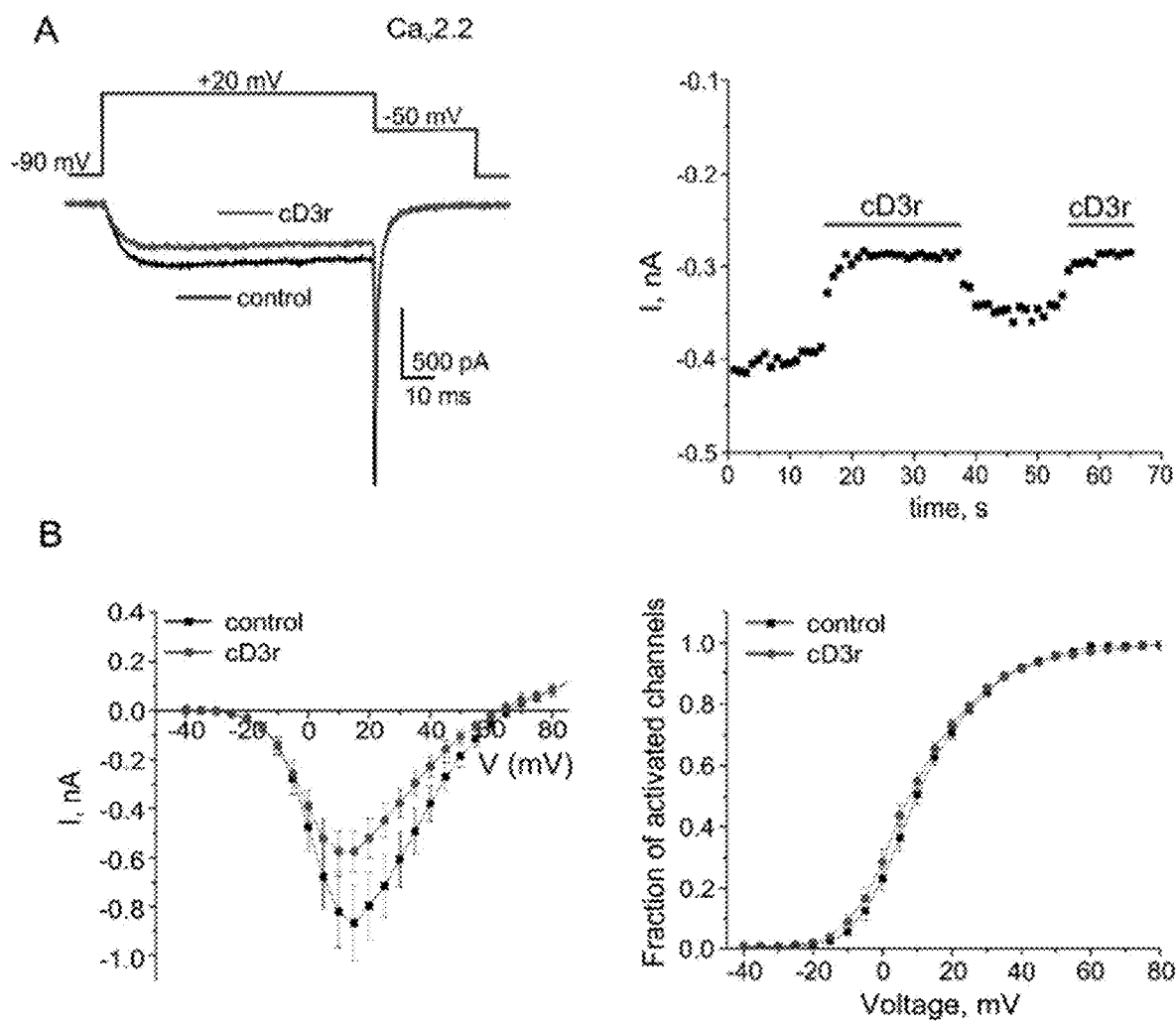
FIG. 7A is a representative image of current intensity mediated by a CaV2.2 channel before and after exposure to cD3r as set forth in Example 3 below.
FIG. 7B shows the average current intensity to voltage ratio of CaV2.2 expressing cells with and without presence of cD3r as set forth in Example 3 below.
Figures 7C, 7D:
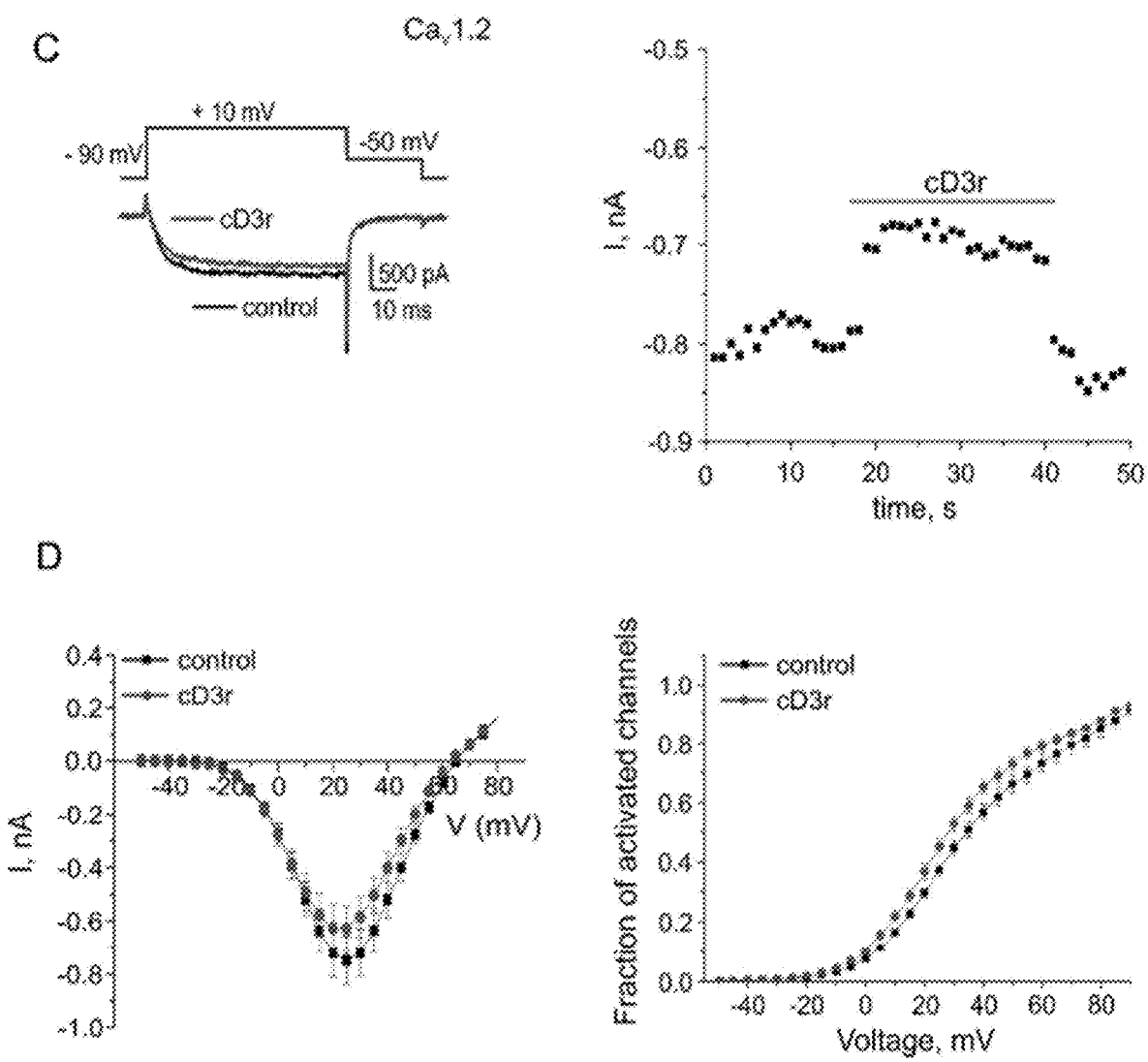
FIG. 7C shows representative ion current discharges mediated by the CaV2.1 channel before and after exposure to cD3r as set forth in Example 3 below.
FIG. 7D shows the average current density to voltage ratio with and without presence of cD3r and the activation curve of CaV2.1 expressing cells as set forth in Example 3 below.

Summary of the effects of cD3r and cRD2r on the Cav2.2 and Cav1.2 channel (FIG. 6). The two bar charts summarize the average ion currents taken from the current intensity-voltage diagrams at +20 mV for the Cav2.2 and +10 mV for the Cav1.2. **$p \leq 0.01$ Effect of cD3r on the CaV2.2 and the CaV1.2 Channel (FIG. 7).

Representative ion current discharges mediated by the CaV2.2 channel were triggered during a 40 ms pulse of −90 mV to +20 mV before and after exposure to 150 nM of cD3r (7A, left diagram). The right diagram 7A shows the course over time of the blockade in a representative cell during successive pulses of −90 mV to +20 m every five seconds. 7B: Average current intensity to voltage ratio of CaV2.2 expressing cells with and without the presence of cD3r (n=8) and fraction of activated channels versus voltage (activation curve). 7C: Representative ion current discharges mediated by the CaV2.1 channel were triggered during a 40 ms pulse of −90 mV to +20 mV before and after exposure to 150 nM of cD3r (7C, left diagram). The right diagram 7C shows the course over time of the blockade in a representative cell during successive pulses of −90 mV to +20 m every five seconds. 7D: Average current intensity to voltage ratio with and without the presence of cD3r (n=8) and activation curve of CaV2.1 expressing cells (n=7).

Figures 8A, 8B:
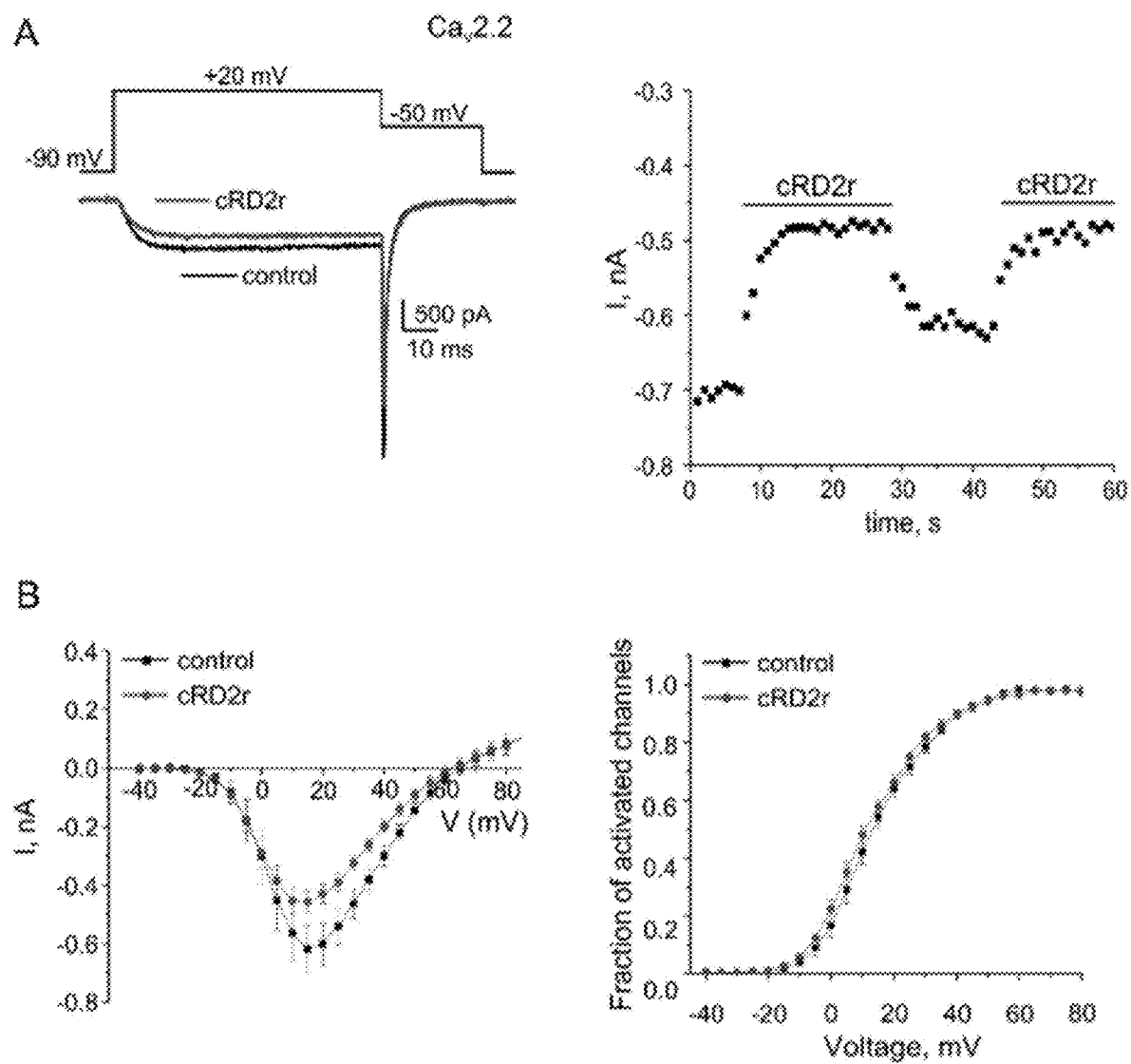
FIG. 8A is a representative image of current discharges mediated by a CaV2.2 channel before and after exposure to cRD2r as set forth in Example 3 below; expressing cells with and without presence of cRD2r and fraction of activated channels versus voltage as set forth in Example 3 below.
Figures 8C, 8D:
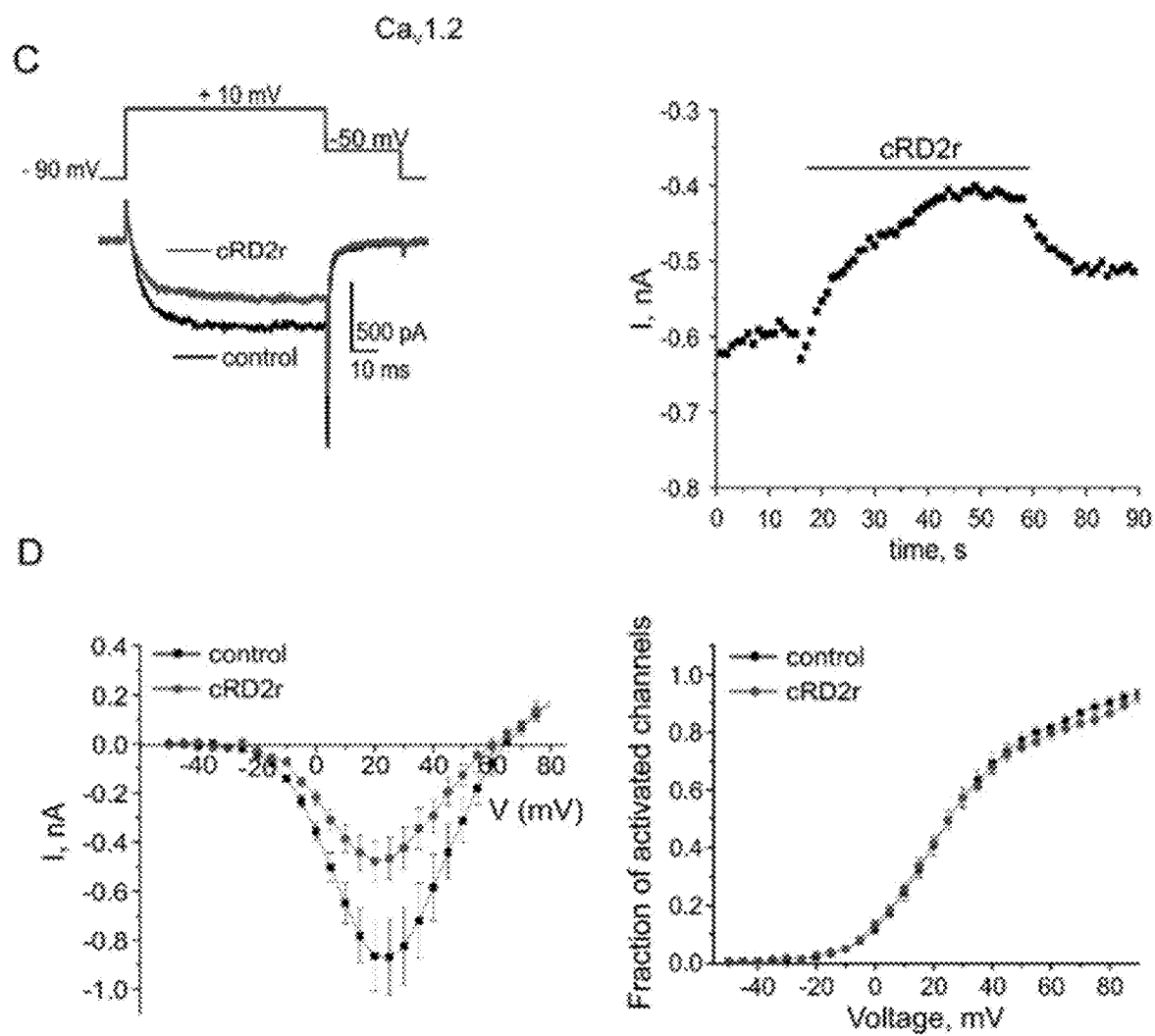
FIG. 8C shows representative ion current discharges mediated by the CaV2.1 channel before and after exposure to cRD2r and the course over time of the blockade in a representative cell during successive voltage pulses as set forth in Example 3 below.
FIG. 8D shows the average current density to voltage ratio with and without presence of cRD2r and the activation curve of CaV2.1 expressing cells as set forth in Example 3 below.

Effect of cRD2r on the CaV2.2 and the CaV1.2 Channel (FIG. 8).

8A: Representative ion current discharges mediated by the CaV2.2 channel were triggered during a 40 ms pulse of −90 mV to +20 mV before and after exposure to 150 nM cRD2r (8A, left diagram). The right diagram 8A shows the course over time of the blockade in a representative cell during successive pulses of −90 mV to +20 m every five seconds. 8B: Average current intensity to voltage ratio of CaV2.2 expressing cells with and without the presence of cRD2r (n=7) and fraction of activated channels versus voltage (activation curve). 8C: Representative ion current discharges mediated by the CaV2.1 channel were triggered during a 40 ms pulse of −90 mV to +20 mV before and after exposure to 150 nM of cRD2r (left diagram). The right diagram 8C shows the course over time of the blockade in a representative cell during successive pulses of −90 mV to +20 m every five seconds. 8D: Average current intensity to voltage ratio with and without the presence of cRD2r (n=8) and activation curve of CaV2.1 expressing cells (n=6).

What is claimed is:

1. A method of treating pain mediated by N-type neuronal calcium channels (NCCs), wherein the method comprises administering to a subject in need thereof a therapeutically effective amount of a composition consisting of or comprising one or both of peptides "RD2" (SEQ ID NO: 1) and "D3" (SEQ ID NO: 2) and/or a polymer comprising one or both of RD2 (SEQ ID NO: 1) and D3 (SEQ ID NO: 2), thereby reducing the pain mediated by NCCs in the subject when compared to no treatment with the composition.

2. The method of claim 1, wherein chronic pain is treated.

3. The method of claim 1, wherein neuropathic pain is treated.

4. The method of claim 1, wherein NCCs the N-type neuronal calcium channels (NCCs) are blocked.

5. The method of claim 1, wherein the peptides are composed essentially of D-enantiomers.

6. The method of claim 1, wherein the composition comprises RD2 (SEQ ID NO: 1) and/or a polymer comprising RD2 (SEQ ID NO: 1).

7. The method of claim 1, wherein the composition comprises D3 (SEQ ID NO: 2) and/or a polymer comprising D3 (SEQ ID NO: 2).

8. The method of claim 1, wherein the peptides are administered in a dose of from 1 µg to 1 g per kilo of body weight.

9. The method of claim 1, wherein the composition is administered by one or more of intravenous, subcutaneous, intraperitoneal, intranasal or oral administration.

10. The method of claim 1, wherein the composition is administered orally.

11. The method of claim 4, wherein the composition has an $IC_{50}$ value of 1 nanomolar to 1 millimolar for N-type NCCs.

12. A method of reducing the release of neurotransmitters associated with pain and mediated by N-type neuronal calcium channels (NCCs) in a subject in need thereof, wherein the method comprises contacting the NCCs in the subject with a composition consisting of or comprising one or both of peptides RD2 (SEQ ID NO: 1) and D3 (SEQ ID NO: 2) and/or a polymer comprising one or both of RD2

(SEQ ID NO: 1) and D3 (SEQ ID NO: 2) for use as an analgesic in the subject in need thereof, thereby reducing the release of neurotransmitters associated with pain and mediated by NCCs in the subject when compared to no treatment with the composition.

13. The method of claim 12, wherein a calcium influx through the NCC in the subject is reduced compared to a control subject with no treatment with the composition.

14. The method of claim 13, wherein the function of L-type NCCs in the subject is not modified when compared to a control subject with no treatment with the composition.

15. A method of inhibiting an N-type NCC in a subject in need thereof, wherein the method comprises contacting the N-type NCC in the subject in need thereof with a composition consisting of or comprising one or both of peptides RD2 (SEQ ID NO: 1) and D3 (SEQ ID NO: 2) and/or a polymer comprising one or both of RD2 (SEQ ID NO: 1) and D3 (SEQ ID NO: 2), thereby inhibiting the N-type NCC in the subject when compared to no treatment with the composition.

16. The method of claim 15, wherein the function of L-type NCCs in the subject is not modified when compared to a control subject with no treatment with the composition.

\* \* \* \* \*

SEQUENCE LISTING

```
<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 1

Pro Thr Leu His Thr His Asn Arg Arg Arg Arg Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(12)
<223> OTHER INFORMATION: D-amino acid

<400> SEQUENCE: 2

Arg Pro Arg Thr Arg Leu His Thr His Arg Asn Arg
1               5                   10
```

<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide
<220> FEATURE:
<221> NAME/KEY: MOD_RES
<222> LOCATION: (1)..(24)
<223> OTHER INFORMATION: D-amino acid

<400> SEQUENCE: 3

Pro Thr Leu His Thr His Asn Arg Arg Arg Arg Arg Pro Thr Leu His
1               5                   10                  15

Thr His Asn Arg Arg Arg Arg Arg
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(24)
<223> OTHER INFORMATION: D-amino acid

<400> SEQUENCE: 4

Pro Thr Leu His Thr His Asn Arg Arg Arg Arg Arg Pro Arg Thr
1               5                   10                  15

Arg Leu His Thr His Arg Asn Arg
            20

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid

<400> SEQUENCE: 5

Arg Pro Arg Thr Arg Leu His Thr His Arg Asn Arg Arg
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid

<400> SEQUENCE: 6

Arg Pro Arg Thr Arg Leu His Thr His Arg Asn Arg Pro

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid

<400> SEQUENCE: 7

Arg Pro Arg Thr Arg Leu His Thr His Arg Asn Arg Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK1
<220> FEATURE:
<221> NAME/KEY: MOD_RES
<222> LOCATION: (1)..(12)
<223> OTHER INFORMATION: D-amino acid

<400> SEQUENCE: 8

Arg Lys Arg Ile Arg Leu Val Tyr His Ile Asn Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK2 (with phenylglycine (D) in
      position 7 instead of glycine)
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: D-phenylglycine
<220> FEATURE:
<221> NAME/KEY: MOD_RES
<222> LOCATION: (8)..(12)
<223> OTHER INFORMATION: D-amino acid

<400> SEQUENCE: 9

Arg Lys Arg Ile Arg Leu Gly Tyr His Ile Asn Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK3 (with phenylglycine (D) in
```

-continued

```
      position 7 instead of glycine)
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: D-phenylglycine
<220> FEATURE:
<221> NAME/KEY: MOD_RES
<222> LOCATION: (8)..(12)
<223> OTHER INFORMATION: D-amino acid

<400> SEQUENCE: 10

Arg Lys Arg Ile Arg Leu Gly Tyr His Trp Asn Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK4
<220> FEATURE:
<221> NAME/KEY: MOD_RES
<222> LOCATION: (1)..(12)
<223> OTHER INFORMATION: D-amino acid

<400> SEQUENCE: 11

Arg Lys Arg Ile Arg Leu Val Tyr His Trp Asn Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK5
<220> FEATURE:
<221> NAME/KEY: MOD_RES
<222> LOCATION: (1)..(12)
<223> OTHER INFORMATION: D-amino acid

<400> SEQUENCE: 12

Arg Lys Arg Val Arg Leu Val Tyr His Lys Lys Arg
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK6
<220> FEATURE:
<221> NAME/KEY: MOD_RES
<222> LOCATION: (1)..(12)
<223> OTHER INFORMATION: D-amino acid

<400> SEQUENCE: 13

Arg Lys Arg Ile Arg Leu Val Thr Lys Lys Lys Arg
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK7 with 4-fluoro-phenylalanine (D)
      in position 7 instead of phenylalanine)
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: D-4-fluorophenylalanine
<220> FEATURE:
<221> NAME/KEY: MOD_RES
<222> LOCATION: (8)..(12)
<223> OTHER INFORMATION: D-amino acid

<400> SEQUENCE: 14

Arg Lys Arg Val Arg Leu Phe Thr His Ile Lys Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK15 (with phenylglycine (D) in
      position 7 instead of glycine)
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: D-phenylglycine
<220> FEATURE:
<221> NAME/KEY: MOD_RES
<222> LOCATION: (8)..(12)
<223> OTHER INFORMATION: D-amino acid

<400> SEQUENCE: 15

Arg Pro Arg Val Arg Leu Gly Tyr His Trp Asn Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK16 (with homoarginine (D) in
      position 4 instead of arginine)
<220> FEATURE:
<221> NAME/KEY: MOD_RES
<222> LOCATION: (1)..(3)
<223> OTHER INFORMATION: D-amino acid
<220> FEATURE:
<221> NAME/KEY: MOD_RES
<222> LOCATION: (4)..(4)
<223> OTHER INFORMATION: D-homoarginine
<220> FEATURE:
<221> NAME/KEY: MOD_RES
```

```
<222> LOCATION: (5)..(12)
<223> OTHER INFORMATION: D-amino acid

<400> SEQUENCE: 16

Arg Lys Arg Arg Arg Leu Val Thr Lys Arg Asn Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK17 (with phenylglycine (D) in
      position 7 instead of glycine)
<220> FEATURE:
<221> NAME/KEY: MOD_RES
<222> LOCATION: (1)..(6)
<223> OTHER INFORMATION: D-amino acid
<220> FEATURE:
<221> NAME/KEY: MOD_RES
<222> LOCATION: (7)..(7)
<223> OTHER INFORMATION: D-phenylglycine
<220> FEATURE:
<221> NAME/KEY: MOD_RES
<222> LOCATION: (8)..(12)
<223> OTHER INFORMATION: D-amino acid

<400> SEQUENCE: 17

Arg Lys Arg Ile Arg Leu Gly Tyr His Ile Lys Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: D-Peptide, ANK18 (with homoarginine (D) in
      position 4 instead of arginine)
<220> FEATURE:
<221> NAME/KEY: MOD_RES
<222> LOCATION: (1)..(3)
<223> OTHER INFORMATION: D-amino acid
<220> FEATURE:
<221> NAME/KEY: MOD_RES
<222> LOCATION: (4)..(4)
<223> OTHER INFORMATION: D-homoarginine
<220> FEATURE:
<221> NAME/KEY: MOD_RES
<222> LOCATION: (5)..(12)
<223> OTHER INFORMATION: D-amino acid

<400> SEQUENCE: 18

Arg Pro Arg Arg Arg Leu His Thr Lys Lys Lys Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid
```

```
<400> SEQUENCE: 19

Pro Thr Leu His Thr His Asn Arg Arg Arg Arg Arg
1               5                   10

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(24)
<223> OTHER INFORMATION: D-amino acid
<220> FEATURE:
<221> NAME/KEY: MISC_FEATURE
<222> LOCATION: (1)..(24)
<223> OTHER INFORMATION: Cyclized peptide

<400> SEQUENCE: 20

Pro Thr Leu His Thr His Asn Arg Arg Arg Arg Pro Thr Leu His
1               5                   10                  15

Thr His Asn Arg Arg Arg Arg Arg
            20

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid
<220> FEATURE:
<221> NAME/KEY: MISC_FEATURE
<222> LOCATION: (1)..(13)
<223> OTHER INFORMATION: Cyclized peptide

<400> SEQUENCE: 21

Arg Pro Arg Thr Arg Leu His Thr His Arg Asn Arg Arg
1               5                   10
```